United States Patent
Li et al.

(10) Patent No.: US 7,952,718 B2
(45) Date of Patent: May 31, 2011

(54) HIGH RESOLUTION OPTICAL COHERENCE TOMOGRAPHY BASED IMAGING FOR INTRALUMINAL AND INTERSTITIAL USE IMPLEMENTED WITH A REDUCED FORM FACTOR

(75) Inventors: Xingde Li, Seattle, WA (US); Xiumei Liu, Fremont, CA (US); Joo Ha Hwang, Bellevue, WA (US)

(73) Assignee: University of Washington, Seattle, WA (US)

( * ) Notice: Subject to any disclaimer, the term of this patent is extended or adjusted under 35 U.S.C. 154(b) by 512 days.

(21) Appl. No.: 12/114,281

(22) Filed: May 2, 2008

(65) Prior Publication Data
US 2009/0323076 A1    Dec. 31, 2009

Related U.S. Application Data

(60) Provisional application No. 60/915,903, filed on May 3, 2007.

(51) Int. Cl.
*G01B 9/02* (2006.01)
(52) U.S. Cl. ...................................................... 356/479
(58) Field of Classification Search ............. 250/227.19, 250/227.27; 356/456, 477, 479, 497; 385/12
See application file for complete search history.

(56) References Cited

U.S. PATENT DOCUMENTS

| | | | |
|---|---|---|---|
| 4,118,270 A | 10/1978 | Pan et al. | 156/659 |
| 4,234,788 A | 11/1980 | Palmer et al. | 250/227 |
| 4,265,699 A | 5/1981 | Ladany | 156/657 |
| 4,410,235 A | 10/1983 | Klement et al. | 350/96.18 |
| 4,454,547 A | 6/1984 | Yip et al. | 358/293 |
| 4,686,963 A | 8/1987 | Cohen et al. | 128/4 |
| 4,688,555 A | 8/1987 | Wardle | 128/4 |
| 4,695,163 A | 9/1987 | Schachar | 356/369 |

(Continued)

FOREIGN PATENT DOCUMENTS
DE    4428967    12/1995
(Continued)

OTHER PUBLICATIONS

Barhoum et al., "Optical modeling of an ultrathin scanning fiber endoscope, a preliminary study of confocal versus non-confocal detection." *Optics Express*, vol. 13, No. 19: 7548-7562, Sep. 19, 2005.

(Continued)

*Primary Examiner* — Gregory J Toatley
*Assistant Examiner* — Scott M Richey
(74) *Attorney, Agent, or Firm* — Ronald M. Anderson

(57) ABSTRACT

Mechanically robust minimal form factor OCT probes suitable for medical applications such as needle biopsy, intraluminal and intravascular imaging are achieved in part by employing compound lenses with some or all of the optical elements, including an optical fiber, to be thermally fused in tandem. To achieve a desired working distance without increasing a diameter of the optics assembly, a spacer can be disposed between the optical fiber and focusing optics. The compound lens configuration can achieve higher transverse resolution compared to a single lens at a desired working distance without increasing the probe diameter. In exemplary needle biopsy embodiments, the optical assembly is encapsulated in a glass housing or metal-like housing with a glass window, which is then selectively passed through a hollow needle. Esophageal imaging embodiments are combined with a balloon catheter. Circumferential and three-dimensional spiral scanning can be achieved in each embodiment.

29 Claims, 11 Drawing Sheets

U.S. PATENT DOCUMENTS

| | | | | |
|---|---|---|---|---|
| 4,710,619 A | 12/1987 | Haberl | | 250/203 |
| 4,743,283 A | 5/1988 | Borsuk | | 65/2 |
| 4,758,222 A | 7/1988 | McCoy | | 604/95 |
| 4,762,118 A | 8/1988 | Lia et al. | | 128/4 |
| 4,768,513 A | 9/1988 | Suzuki | | 600/476 |
| 4,782,228 A | 11/1988 | Westell | | 250/236 |
| 4,804,395 A | 2/1989 | Clark et al. | | 65/2 |
| 4,824,195 A | 4/1989 | Khoe | | 350/96.18 |
| 4,850,364 A | 7/1989 | Leavitt | | 600/455 |
| 4,928,316 A | 5/1990 | Heritage et al. | | 398/199 |
| 4,979,496 A | 12/1990 | Komi | | 128/4 |
| 4,983,165 A | 1/1991 | Loiterman | | 604/95 |
| 5,037,174 A | 8/1991 | Thompson | | 385/33 |
| 5,074,642 A | 12/1991 | Hicks | | 385/116 |
| 5,103,497 A | 4/1992 | Hicks | | 385/117 |
| 5,172,685 A | 12/1992 | Nudelman | | 600/108 |
| 5,209,117 A | 5/1993 | Bennett | | 73/517 |
| 5,231,286 A | 7/1993 | Kajimura et al. | | 250/234 |
| 5,247,174 A | 9/1993 | Berman | | 250/235 |
| 5,272,330 A | 12/1993 | Betzig et al. | | 250/216 |
| 5,286,970 A | 2/1994 | Betzig et al. | | 250/227.26 |
| 5,305,759 A | 4/1994 | Kaneko et al. | | 600/476 |
| 5,321,501 A * | 6/1994 | Swanson et al. | | 356/479 |
| 5,360,968 A | 11/1994 | Scott | | 235/454 |
| 5,381,782 A | 1/1995 | DeLaRama et al. | | 128/4 |
| 5,394,500 A | 2/1995 | Marchman | | 385/123 |
| 5,405,337 A | 4/1995 | Maynard | | 604/281 |
| 5,425,123 A | 6/1995 | Hicks | | 385/117 |
| 5,459,803 A | 10/1995 | Yamane et al. | | 385/33 |
| 5,480,046 A | 1/1996 | Filas et al. | | 216/7 |
| 5,507,725 A | 4/1996 | Savage et al. | | 604/95 |
| 5,512,035 A | 4/1996 | Konstorum et al. | | 600/146 |
| 5,535,759 A | 7/1996 | Wilk | | 128/898 |
| 5,549,542 A | 8/1996 | Kovalcheck | | 600/146 |
| 5,563,969 A | 10/1996 | Honmou | | 385/35 |
| 5,570,441 A | 10/1996 | Filas et al. | | 385/43 |
| 5,627,922 A | 5/1997 | Kopelman et al. | | 385/12 |
| 5,643,175 A | 7/1997 | Adair | | 600/133 |
| 5,649,897 A | 7/1997 | Nakamura | | 600/111 |
| 5,668,644 A | 9/1997 | Kuroiwa et al. | | 358/480 |
| 5,703,979 A | 12/1997 | Filas et al. | | 385/43 |
| 5,715,337 A | 2/1998 | Spitzer et al. | | 385/4 |
| 5,724,169 A | 3/1998 | LaGasse | | 398/141 |
| 5,727,098 A | 3/1998 | Jacobson | | 385/31 |
| 5,765,561 A | 6/1998 | Chen et al. | | 128/653.1 |
| 5,894,122 A | 4/1999 | Tomita | | 250/234 |
| 5,906,620 A | 5/1999 | Nakao et al. | | 606/113 |
| 5,919,200 A | 7/1999 | Stambaugh et al. | | 606/159 |
| 5,939,709 A | 8/1999 | Ghislain et al. | | 250/216 |
| 5,947,905 A | 9/1999 | Hadjicostis et al. | | 600/463 |
| 5,984,860 A | 11/1999 | Shan | | 600/116 |
| 5,991,697 A | 11/1999 | Nelson et al. | | 702/49 |
| 6,035,229 A | 3/2000 | Silverstein et al. | | 600/473 |
| 6,046,720 A | 4/2000 | Melville et al. | | 345/160 |
| 6,069,698 A | 5/2000 | Ozawa et al. | | 356/511 |
| 6,081,605 A | 6/2000 | Roth et al. | | 382/103 |
| 6,091,067 A | 7/2000 | Drobot et al. | | 250/234 |
| 6,096,054 A | 8/2000 | Wyzgala et al. | | 606/170 |
| 6,097,528 A | 8/2000 | Lebby et al. | | 359/251 |
| 6,134,003 A | 10/2000 | Tearney et al. | | 356/479 |
| 6,142,957 A | 11/2000 | Diamond et al. | | 600/567 |
| 6,148,095 A | 11/2000 | Prause et al. | | 382/131 |
| 6,161,035 A | 12/2000 | Furusawa | | 600/476 |
| 6,169,281 B1 | 1/2001 | Chen et al. | | 250/234 |
| 6,185,443 B1 | 2/2001 | Crowley | | 600/407 |
| 6,191,862 B1 | 2/2001 | Swanson et al. | | 356/479 |
| 6,211,904 B1 | 4/2001 | Adair et al. | | 348/76 |
| 6,215,437 B1 | 4/2001 | Schurmann et al. | | 342/42 |
| 6,240,312 B1 | 5/2001 | Alfano et al. | | 600/476 |
| 6,241,657 B1 | 6/2001 | Chen et al. | | 600/117 |
| 6,246,914 B1 | 6/2001 | de la Rama et al. | | 607/122 |
| 6,289,144 B1 | 9/2001 | Neuschafer et al. | | 385/12 |
| 6,294,775 B1 | 9/2001 | Seibel et al. | | 250/208.1 |
| 6,327,493 B1 | 12/2001 | Ozawa et al. | | 600/476 |
| 6,370,422 B1 | 4/2002 | Richards-Kortun et al. | | 600/478 |
| 6,387,119 B2 | 5/2002 | Wolf et al. | | 623/1.11 |
| 6,441,359 B1 | 8/2002 | Cozier et al. | | 250/216 |
| 6,443,894 B1 | 9/2002 | Sumanaweera et al. | | 600/443 |
| 6,461,337 B1 | 10/2002 | Minotti et al. | | 604/264 |
| 6,466,687 B1 | 10/2002 | Uppaluri et al. | | 382/128 |
| 6,485,413 B1 | 11/2002 | Boppart et al. | | 600/160 |
| 6,515,274 B1 | 2/2003 | Moskovits et al. | | 250/216 |
| 6,515,781 B2 | 2/2003 | Lewis et al. | | 359/204 |
| 6,525,310 B2 | 2/2003 | Dunfield | | 250/235 |
| 6,545,260 B1 | 4/2003 | Katashiro | | 250/227.26 |
| 6,546,271 B1 | 4/2003 | Reisfeld | | 600/407 |
| 6,549,801 B1 | 4/2003 | Chen et al. | | 600/425 |
| 6,550,918 B1 | 4/2003 | Agostinelli et al. | | 353/7 |
| 6,563,105 B2 | 5/2003 | Seibel et al. | | 250/208.1 |
| 6,563,998 B1 | 5/2003 | Farah et al. | | 385/131 |
| 6,564,087 B1 | 5/2003 | Pitris et al. | | 600/478 |
| 6,564,089 B2 * | 5/2003 | Izatt et al. | | 600/478 |
| 6,612,980 B2 | 9/2003 | Chen et al. | | 600/117 |
| 6,615,072 B1 * | 9/2003 | Izatt et al. | | 600/478 |
| 6,678,541 B1 | 1/2004 | Durkin et al. | | 600/310 |
| 6,685,718 B1 | 2/2004 | Wyzgala et al. | | 606/170 |
| 6,687,010 B1 | 2/2004 | Horii et al. | | 356/479 |
| 6,689,064 B2 | 2/2004 | Hager et al. | | 600/454 |
| 6,690,963 B2 | 2/2004 | Ben-Haim et al. | | 600/424 |
| 6,694,983 B2 | 2/2004 | Wolf et al. | | 128/898 |
| 6,735,463 B2 | 5/2004 | Izatt et al. | | 600/476 |
| 6,755,532 B1 | 6/2004 | Cobb | | 353/7 |
| 6,773,394 B2 | 8/2004 | Taniguchi et al. | | 600/117 |
| 6,779,892 B2 | 8/2004 | Agostinelli et al. | | 353/7 |
| 6,785,571 B2 | 8/2004 | Glossop | | 600/424 |
| 6,788,967 B2 | 9/2004 | Ben-Haim et al. | | 600/424 |
| 6,818,001 B2 | 11/2004 | Wulfman et al. | | 606/159 |
| 6,826,342 B1 | 11/2004 | Bise et al. | | 385/125 |
| 6,832,984 B2 | 12/2004 | Stelzer et al. | | 604/93.01 |
| 6,836,560 B2 | 12/2004 | Emery | | 382/145 |
| 6,839,586 B2 | 1/2005 | Webb | | 600/478 |
| 6,845,190 B1 | 1/2005 | Smithwick et al. | | 385/25 |
| 6,858,005 B2 | 2/2005 | Ohline et al. | | 600/141 |
| 6,872,433 B2 | 3/2005 | Seward et al. | | 428/36.9 |
| 6,882,429 B1 | 4/2005 | Weitekamp et al. | | 356/482 |
| 6,889,175 B2 | 5/2005 | Green | | 702/190 |
| 6,892,090 B2 | 5/2005 | Verard et al. | | 600/424 |
| 6,895,270 B2 | 5/2005 | Ostrovsky | | 600/476 |
| 6,902,528 B1 | 6/2005 | Garibaldi et al. | | 600/118 |
| 6,932,829 B2 | 8/2005 | Majercak | | 606/198 |
| 6,975,898 B2 | 12/2005 | Seibel | | 600/473 |
| 7,004,173 B2 | 2/2006 | Sparks et al. | | 128/898 |
| 7,023,558 B2 | 4/2006 | Fee et al. | | 356/489 |
| 7,038,191 B2 | 5/2006 | Kare et al. | | 250/227.11 |
| 7,072,046 B2 | 7/2006 | Xie et al. | | 356/479 |
| 7,158,234 B2 | 1/2007 | Uchiyama et al. | | 356/479 |
| 7,170,610 B2 | 1/2007 | Knuttel | | 356/456 |
| 7,179,220 B2 | 2/2007 | Kukuk | | 600/118 |
| 7,189,961 B2 | 3/2007 | Johnston et al. | | 250/234 |
| 7,252,674 B2 | 8/2007 | Wyzgala et al. | | 606/170 |
| 7,261,687 B2 | 8/2007 | Yang | | 600/173 |
| 7,349,098 B2 | 3/2008 | Li | | 356/479 |
| 7,366,376 B2 * | 4/2008 | Shishkov et al. | | 385/35 |
| 7,404,929 B2 | 7/2008 | Fulghum, Jr. | | 422/82.05 |
| 7,447,408 B2 * | 11/2008 | Bouma et al. | | 385/123 |
| 7,515,274 B2 * | 4/2009 | Gelikonov et al. | | 356/479 |
| 7,530,948 B2 | 5/2009 | Seibel et al. | | 600/102 |
| 7,615,005 B2 | 11/2009 | Stefanchik et al. | | 600/106 |
| 7,616,986 B2 * | 11/2009 | Seibel et al. | | 600/476 |
| 7,747,312 B2 | 6/2010 | Barrick et al. | | 600/426 |
| 7,783,337 B2 * | 8/2010 | Feldman et al. | | 600/407 |
| 2001/0030744 A1 | 10/2001 | Chang et al. | | 356/73 |
| 2001/0055462 A1 | 12/2001 | Seibel | | 385/147 |
| 2002/0064341 A1 | 5/2002 | Fauver et al. | | 385/25 |
| 2002/0071625 A1 | 6/2002 | Bartholomew et al. | | 385/12 |
| 2003/0004412 A1 | 1/2003 | Izatt et al. | | 600/425 |
| 2003/0009189 A1 | 1/2003 | Gilson et al. | | 606/200 |
| 2003/0032878 A1 | 2/2003 | Shahidi | | 600/429 |
| 2003/0045778 A1 | 3/2003 | Ohline et al. | | 600/114 |
| 2003/0055317 A1 | 3/2003 | Taniguchi et al. | | 600/117 |
| 2003/0103199 A1 | 6/2003 | Jung et al. | | 356/73 |
| 2003/0103665 A1 | 6/2003 | Uppaluri et al. | | 382/131 |
| 2003/0142934 A1 | 7/2003 | Pan et al. | | 385/116 |
| 2003/0160721 A1 | 8/2003 | Gilboa et al. | | 342/450 |
| 2003/0179428 A1 | 9/2003 | Suzuki et al. | | 359/204 |
| 2003/0208107 A1 | 11/2003 | Refael | | 600/300 |
| 2003/0208134 A1 | 11/2003 | Secrest et al. | | 600/562 |

| | | | | |
|---|---|---|---|---|
| 2003/0216639 | A1 | 11/2003 | Gilboa et al. | 600/424 |
| 2003/0220749 | A1 | 11/2003 | Chen et al. | 702/31 |
| 2003/0236564 | A1 | 12/2003 | Majercak | 623/1.11 |
| 2004/0015049 | A1 | 1/2004 | Zaar | 600/101 |
| 2004/0015053 | A1 | 1/2004 | Bieger et al. | 600/117 |
| 2004/0033006 | A1 | 2/2004 | Farah | 385/14 |
| 2004/0061072 | A1 | 4/2004 | Gu et al. | 250/458.1 |
| 2004/0118415 | A1 | 6/2004 | Hall et al. | 128/898 |
| 2004/0147827 | A1 | 7/2004 | Bowe | 600/374 |
| 2004/0176683 | A1 | 9/2004 | Whitin et al. | 600/424 |
| 2004/0181148 | A1 | 9/2004 | Uchiyama et al. | 600/425 |
| 2004/0199052 | A1 | 10/2004 | Banik et al. | 600/142 |
| 2004/0243227 | A1 | 12/2004 | Starksen et al. | 623/2.11 |
| 2004/0249267 | A1 | 12/2004 | Gilboa | 600/204 |
| 2004/0260199 | A1 | 12/2004 | Hardia et al. | 600/566 |
| 2005/0020878 | A1 | 1/2005 | Ohnishi et al. | 600/117 |
| 2005/0020926 | A1 | 1/2005 | Wiklof et al. | 600/476 |
| 2005/0036150 | A1 | 2/2005 | Izatt et al. | 356/479 |
| 2005/0054931 | A1 | 3/2005 | Clark | 600/453 |
| 2005/0065433 | A1 | 3/2005 | Anderson | 600/424 |
| 2005/0085146 | A1 | 4/2005 | Belson et al. | 600/146 |
| 2005/0111009 | A1 | 5/2005 | Keightley et al. | 356/602 |
| 2005/0168751 | A1 | 8/2005 | Horii et al. | 356/479 |
| 2005/0171438 | A1 | 8/2005 | Chen et al. | 600/476 |
| 2005/0171592 | A1 | 8/2005 | Majercak | 623/1.11 |
| 2005/0183733 | A1 | 8/2005 | Kawano et al. | 128/899 |
| 2005/0206774 | A1 | 9/2005 | Tsujimoto | 348/345 |
| 2005/0215854 | A1 | 9/2005 | Ozaki et al. | 600/109 |
| 2005/0215911 | A1 | 9/2005 | Alfano et al. | 600/476 |
| 2005/0228290 | A1 | 10/2005 | Borovsky et al. | 600/466 |
| 2005/0250983 | A1 | 11/2005 | Tremaglio et al. | 600/101 |
| 2005/0272975 | A1 | 12/2005 | McWeeney et al. | 600/113 |
| 2006/0015126 | A1 | 1/2006 | Sher | 606/159 |
| 2006/0030753 | A1 | 2/2006 | Boutillette et al. | 600/146 |
| 2006/0052662 | A1 | 3/2006 | Kress | 600/123 |
| 2006/0066865 | A1 | 3/2006 | Tsujita | 356/479 |
| 2006/0100480 | A1 | 5/2006 | Ewers et al. | 600/114 |
| 2006/0106317 | A1 | 5/2006 | McConnell et al. | 600/476 |
| 2006/0126064 | A1 | 6/2006 | Bambot et al. | 356/337 |
| 2006/0149134 | A1 | 7/2006 | Soper et al. | 600/182 |
| 2006/0149163 | A1 | 7/2006 | Hibner et al. | 600/566 |
| 2006/0165350 | A1* | 7/2006 | Gelikonov et al. | 385/33 |
| 2006/0187462 | A1 | 8/2006 | Srinivasan et al. | 356/479 |
| 2006/0202115 | A1 | 9/2006 | Lizotte et al. | 250/234 |
| 2006/0241495 | A1 | 10/2006 | Kurtz | 600/476 |
| 2006/0252993 | A1 | 11/2006 | Freed et al. | 600/146 |
| 2007/0038119 | A1 | 2/2007 | Chen et al. | 600/476 |
| 2007/0066983 | A1 | 3/2007 | Maschke | 606/159 |
| 2007/0088219 | A1 | 4/2007 | Xie et al. | 600/473 |
| 2007/0093703 | A1 | 4/2007 | Sievert et al. | 600/343 |
| 2007/0129601 | A1 | 6/2007 | Johnston et al. | 600/109 |
| 2007/0213618 | A1 | 9/2007 | Li et al. | 600/476 |
| 2007/0270650 | A1 | 11/2007 | Eno et al. | 600/145 |
| 2008/0004491 | A1 | 1/2008 | Karasawa | 600/101 |
| 2008/0221388 | A1 | 9/2008 | Seibel et al. | 600/109 |

FOREIGN PATENT DOCUMENTS

| | | |
|---|---|---|
| EP | 0 713 672 | 5/1996 |
| EP | 0 520 388 | 9/1996 |
| EP | 1 077 360 | 2/2001 |
| EP | 1 088 515 | 4/2001 |
| EP | 1 142 529 A1 | 10/2001 |
| EP | 0 712 032 | 12/2001 |
| EP | 1 310 206 | 5/2003 |
| EP | 1 421 913 | 5/2004 |
| EP | 0 910 284 | 1/2007 |
| EP | 1 063 921 | 2/2007 |
| JP | 05-154154 | 6/1993 |
| JP | 06-511312 | 12/1994 |
| JP | 2001174744 A2 | 6/2001 |
| WO | WO 93/20742 | 10/1993 |
| WO | WO 96/02184 | 2/1996 |
| WO | WO 98/38907 | 9/1998 |
| WO | WO 98/43530 | 10/1998 |
| WO | WO 99/04301 | 1/1999 |
| WO | WO 01/97902 | 12/2001 |
| WO | WO 2005/024496 | 3/2005 |

OTHER PUBLICATIONS

Barnard et al., "Mode Transforming Properties of Tapered Single-mode Fiber Microlens." *Appl. Opt.* vol. 32, No. 12: 2090-2094, Apr. 20, 1993.

Barnard et al., "Single-mode Fiber Microlens with Controllable Spot Size." *Appl. Opt.* vol. 30, No. 15: 1958-1962, May 20, 1991.

Borreman et al., "Fabrication of Polymeric Multimode Waveguides and Devices in SU-8 Photoresist Using Selective Polymerization." *Proceedings Symposium IEEE/LEOS* Benelux Chapter, Amsterdam: pp. 83-86, 2002.

Brown et al., "Recognising Panoramas." *Proceedings of the Ninth IEEE International Conference on Computer Vision* 8pp., Apr. 2003.

Brunetaud et al., "Lasers in Digestive Endoscopy." *Journal of Biomedical Optics* vol. 2, No. 1: 42-52, Jan. 1997.

Deschamps et al., "Automatic construction of minimal paths in 3D images: An application to virtual endoscopy." *CARS'99—H.U. Lemke, M.W. Vannier, K. Inamura & A.G. Fannan (Editors) Elsevier Science B.V .*: 151-155, 1999.

Dickensheets et al., "A Scanned Optical Fiber Confocal Microscope." *Three-Dimensional Microscopy* SPIE vol. 2184: 39-47, 1994.

Dickensheets et al., "Micromachined scanning confocal optical microscope." *Optics Letters*, vol. 21, No. 10: 764-766, May 15, 1996.

Finci et al., "Tandem balloon catheter for coronary angioplasty." *Catheter Cardiovascular Diagnosis* vol. 12, No. 6: 421-425, 1986. 2pp Abstract.

Herline et al., "Surface Registration for Use in Interactive, Image-Guided Liver Surgery." *Computer Aided Surgery*, vol. 5: 11-17, 1999.

Higgins et al., "Integrated Bronchoscopic Video Tracking and 3D CT Registration for Virtual Bronchoscopy." *Medical Imaging 2003*, vol. 5031: 80-89, 2003.

Kiesslich et al., "Diagnosing *Helicobacter pylori* in Vivo by Confocal Laser Endoscopy." *Gastroenterology* vol. 128: 2119-2123, 2005.

Kiraly et al., "Three-Dimensional Path Planning for Virtual Bronchoscopy." *IEEE Transactions on Medical Imaging*, vol. 23, No. 9: 1365-1379, Sep. 2004.

Lee et al., "Microlenses on the End of Single-mode Optical Fibers for Laser Applications." *Appl. Opt.* vol. 24, No. 19: 3134-3139, Oct. 1, 1985.

Lewis et al., "Scanned beam medical imager." *MOEMS Display and Imaging System II*, edited by Hakan Urey, David L. Dickensheets, Proceedings of SPIE, Bellingham, WA, vol. 5348: 40-51, 2004.

Liu et al., "3D Navigation for Endoscope by Magnetic Field." *Proceedings of SPIE*, vol. 4556 25-28, 2001.

Mori et al., "A Method for Tracking camera motion of real endoscope by using virtual endoscopy system." *Proceedings of SPIE*: 1-12, 2000. <www.http://www.toriwaki.nuie.nagoya-u.ac.jp> 12pp 1-12.

Murakami et al., "A Miniature Confocal Optical Microscope With Mems Gimbal Scanner." *The 12th International Conference on Solid State Sensors, Actuators and Microsystems* Boston: 587-590, Jun. 8-12, 2003.

Oikawa et al., "Intra-operative Guidance with Real-time Information of Open MRI and Manipulators Using Coordinate-Integration Module." *Proceedings of SPIE*, vol. 5029: 653-660, 2003.

Pagoulatos et al., "Image-based Registration of Ultrasound and Magnetic Resonance Images: A Preliminary Study." *Proceedings of SPIE* , vol. 3976: 156-164, 2000.

Patterson et al., "Applications of time-resolved light scattering measurements to photodynamic therapy dosimetry." *SPIE* vol. 1203, Photodynamic Therapy: Mechanism II: 62-75, 1990.

Pyhtila et al., "Determining nuclear morphology using an improved angle-resolved low coherence interferometry system." *Optics Express*, vol. 11, No. 25: 3473-3484, Dec. 15, 2003.

Pyhtila et al., "Fourier-domain angle-resolved low coherence interferometry through an endoscopic fiber bundle for light-scattering spectroscopy." *Optics Letters*, vol. 31, No. 6: 772-774, Dec. 1, 2005.

Pyhtila et al., "Rapid, depth-resolved light scattering measurements using Fourier domain, angle-resolved low coherence interferometry." *Optical Society of America*: 6pp, 2004.

Russo et al., "Lens-ended Fibers for Medical Applications: A New Fabrication Technique." *Appl. Opt.* vol. 23, No. 19: 3277-3283, Oct. 1, 1984.

Sasaki et al., "Scanning Near-Field Optical Microscope using Cantilever Integrated with Light Emitting Diode, Waveguide, Aperture, and Photodiode." Optical MEMS 2000 Invited Speakers: Advance Program, Sponsored by IEEE Lasers and Electro-Optics Society: 16pp, 2000. Available at <http://www.ieee.org/organizations/society/leos/LEOSCONF/MEMS/omspeak.html.>.

Schwartz et al., "Electromagnetic Navigation during Flexible Bronchoscopy." *Interventional Pulmonology: Respiration*, vol. 70: 516-522, 2003.

Shahidi et al., "Implementation, Calibration and Accuracy Testing of an Image-Enhanced Endoscopy System." *IEEE Transactions on Medical Imaging*, vol. 21, No. 12: 1524-1535, 2002.

Shinagawa et al., "CT-Guided Transbronchial Biopsy Using an Ultrathin Bronchoscopic Navigation." *Chest*, vol. 125, No. 3: 1138-1143, 2003.

Shoji et al., "Camera motion tracking of real endoscope by using virtual endoscopy system and texture information." *Proceedings of SPIE*, vol. 4321: 122-133, 2001.

Skala et al., "Multiphoton Microscopy of Endogenous Fluorescence Differentiates Normal, Precancerous, and Cancerous Squamous Epithelial Tissues." *Cancer Research* vol. 65, No. 4: 1180-1186, Feb. 15, 2005. Available at <www.aacrjournals.org>.

Smithwick et al., "Modeling and Control of the Resonant Fiber Scanner for Laser Scanning Display or Acquisition." *SID 03 Digest*: 1455-1457, 2003.

Solomon et al., "Three-dimensional CT-Guided Bronchoscopy With a Real-Time Electromagnetic Position Sensor," "A Comparison of Two Image Registration Methods." *Chest*, vol. 118, No. 6: 1783-1787, 2000.

Tsai et al., "All-Optical Histology Using Ultrashort Laser Pulses." *Neuron* Cell Press, vol. 39: 27-41, Jul. 3, 2003.

Wang et al., "Deep Reactive Ion Etching of Silicon Using an Aluminum Etching Mask." *Proceedings of SPIE*, vol. 4876: 633-640, 2003.

Wilson et al., "Optical Reflectance and Transmittance of Tissues: Principles and Applications." *IEEE Journal of Quantum Electronics*, vol. 26, No. 12: 2186-2199, Dec. 1990.

Xu et al., "3D Motion Tracking of pulmonary lesions using CT fluoroscopy images for robotically assisted lung biopsy." *Proceedings of SPIE*, vol. 5367: 394-402, 2004.

Yamada et al., "Characteristics of a Hemispherical Microlens for Coupling Between a Semiconductor Laser and Single-Mode Fiber." *IEEE J. Quant. Electron*, vol. QE-16, No. 10: 1067-1072, Oct. 1980.

Yamamoto et al., "Total enteroscopy with a nonsurgical steerable double-balloon method." *Gastrointestinal Endoscopy* vol. 53, No. 2: 216-220, Feb. 2001. Abstract only.

Yelin et al., "Double-clad fiber for endoscopy." *Optics Letters*, vol. 29, No. 20: 2408-2410, Oct. 15, 2004.

Yelin et al., "Three-dimensional miniature endoscopy."*NATURE* vol. 443: 765 plus supplemental information, Oct. 19, 2006. <www.nature.com/nature/journal/v443/n7113/extref/443765a-s2.doc>.

Yoon et al., "Analysis of Electro Active Polymer Bending: A Component in a Low Cost Ultrathin Scanning Endoscope." *Sensors and Actuators A—Physical*: pp. 1-26, Submitted Jan. 13, 2006, Published Jul. 2006.

n.a., "Given® Diagnostic System." The Platform for PillCam™ Endoscopy Given Imaging Ltd.: 4pp, 2001-2004. <http:www.givenimaging.com>.

n.a., "NASA-Inspired Shape-Sensing Fibers Enable Minimally Invasive Surgery." NASA Tech Briefs vol. 32, No. 2: Feb. 12, 14, 2008.

n.a., "NANO™ SU-8 2000 Negative Tone Photoresist Formulations 2002-2025." Micro-Chem: 5pp, © 2001.

Bird, D. and Gu, M., "Two-photon fluorescence endoscopy with a micro-optic scanning head," Optics Letters 28, 1552 (2003).

Chen, Y.C. and X.D. Li. "Dispersion management up to the third order for real-time optical coherence tomography involving a phase or frequency modulator." Optics Express, 12, 5968-5978 (2004).

Chen, Z.P., T.E. Milner, D. Dave, and J.S. Nelson, "Optical Doppler tomographic imaging of fluid flow velocity in highly scattering media." Optics Letters, 22, 64-66 (1997).

Clark, S.W., Ilday, F.O., and Wise, F.W., "Fiber delivery of femtosecond pulses from a Ti:sapphire laser," Optics Letters 26, 1320 (2001).

Drexler, W., U. Morgner, F.X. Kartner, C. Pitris, S.A. Boppart, X.D. Li, E.P. Ippen, and J.G. Fujimoto. "In vivo ultrahigh-resolution optical coherence tomography." Optics Letters, 24, 1221-1223 (1999).

Flusberg, B., Jung, J., Cocker, E., Anderson, E., and Schnitzer, M., "In vivo brain imaging using a portable 3.9 gram two-photon fluorescence microendoscope," Optics Letters 30, 2272 (2005).

Fu, L., Gan, X., and Gu, M., "Nonlinear optical microscopy based on double-clad photonic crystal fibers," Optics Express 13, 5528 (2005).

Gobel, W., Kerr, J.N.D., Nimmerjahn, A., and Helmchen, F., "Miniaturized two-photon microscope based on a flexible coherent fiber bundle and a gradient-index lens objective," Optics Letters 29, 2521 (2004).

Helmchen, F., Fee, M.S., Tank, D.W., and Denk, W., "A miniature head-mounted two-photon microscope: High-resolution brain imaging in freely moving animals," Neuron 31, 903 (2001).

Huang, D., E.A. Swanson, C.P. Lin, J.S. Schuman, W.G. Stinson, W. Chang, M.R. Hee, T. Flotte, K. Gregory, C.A. Puliafito, and J.G. Fujimoto. "Optical Coherence Tomography." Science, 254, 1178-1181 (1991).

Huber, R., M. Wojtkowski, K. Taira, J.G. Fujimoto, and K. Hsu. "Amplified, frequency swept lasers for frequency domain reflectometry and OCT imaging: design and scaling principles." Optics Express vol. 13, No. 9; May 2, 2005; pp. 3513-3528.

Jung, J.C., and Schnitzer, M.J., "Multiphoton endoscopy," Optics Letters 28, 902 (2003).

Lexer, F., C.K. Hitzenberger, W. Drexler, S. Molebny, H. Sattmann, M. Sticker, and A.F. Fercher. "Dynamic coherent focus OCT with depth-independent transversal resolution." Journal of Modern Optics, 46, 541-553 (1999).

Li, X. D., S.A. Boppart, J. Van Dam, H. Mashimo, M. Mutinga, W. Drexler, M. Klein, C. Pitris, M. L. Krinsky, M. E. Brezinski, and J. G. Fujimoto. "Optical Coherence Tomography: Advanced Technology for the Endoscopic Imaging of Barrett's Esophagus" Endoscopy 2000; 32 (12): pp. 921-930.

Liu, X.M., M.J. Cobb, Y.C. Chen, M.B. Kimmey, and X.D. Li. "Rapid-scanning forward-imaging miniature endoscope for real-time optical coherence tomography." Optics Letters, 29, 1763-1765 (2004).

Martinez, O.E., "3000 Times Grating Compressor with Positive Group-Velocity Dispersion—Application to Fiber Compensation in 1.3-1.6 Mu-M Region," IEEE Journal of Quantum Electronics 23, 59 (1987).

Morofke, D., Michael C. Kolios, I. Alex Vitkin, and Victor X.D. Yang. "Wide dynamic range detection of bidirectional flow in Doppler optical coherence tomography using a two-dimensional Kasai estimator." Optics Letters vol. 32, No. 3; Feb. 1, 2007; pp. 253-255.

Myaing, M.T., Ye, J.Y., Norris, T.B., Thomas, T., Baker, J.R., Wadsworth, W.J., Bouwmans, G., Knight, J.C., and Russell, P.S.J., "Enhanced two-photon biosensing with double-clad photonic crystal fibers," Optics Letters 28, 1224 (2003).

Ohmi, M., T. Kurata, M. Sekimoto, and M. Haruna. "Quasi in-focus optical coherence tomography." Japanese Journal of Applied Physics Part 1—Regular Papers Short Notes & Review Papers, 43, 845-849 (2004).

Podoleanu, A.G., J.A. Rogers, and D.A. Jackson. "Three dimensional OCT images from retina and skin." Optics Express, 7, 292-298 (2000).

Qi, B., A.P. Himmer, L.M. Gordon, X.D.V. Yang, L.D. Dickensheets, and I.A. Vitkin. "Dynamic focus control in high-speed optical coherence tomography based on a microelectromechanical mirror." Optics Communications, 232, 123-128 (2004).

Schmitt, J.M., S.L. Lee, and K.M. Yung. "An optical coherence microscope with enhanced resolving power in thick tissue." Optics Communications, 142, 203-207 (1997).

Seibel, E.J., and Smithwick, Q.Y.J., "Unique features of optical scanning, single fiber endoscopy," Lasers in Surgery and Medicine 30, 177-183 (2002).

Shiraishi, K., A. Ogura, and N. Hiraguri. "Spot Size Reducer for Standard Single-Mode Fibers Utilizing a Graded-Index Fiber Tip" ECOC 97, Sep. 22-25, 1997.

Srivastava, S., "Computer-Aided Identification of Ovarian Cancer in Confocal Microendoscope Images," Department of Electrical and Computer Engineering, University of Arizona Graduate School, (2004).

Tearney, G.J., M.E. Brezinski, J.F. Southern, B.E. Bouma, M.R. Hee, and J.G. Fujimoto. "Determination of the Refractive-Index of Highly Scattering Human Tissue by Optical Coherence Tomography." Optics Letters, 20, 2258-2260 (1995).

Vakoc, Benjamin J., Milen Shishko, Seok H. Yun, Wang-Yuhl Oh, Melissa J. Suter, Adrien Desjardins, John A. Evans, Norman S. Nishioka, Guillermo J. Tearney, and Brett E. Bouma. "Comprehensive esophageal microscopy by using optical frequency-domain imaging (with video)" Gastrointestinal Endoscopy, vol. 65, No. 6: 2007, pp. 898-905.

Yang, Victor X.D., Maggie L. Gordon, Bing Qi, Julius Pekar, Stuart Lo, Emily Seng-Yue, Alvin Mok, Brian C. Wilson, and I. Alex Vitkin. "High speed, wide velocity dynamic range Doppler optical coherence tomography (Part I): System design, signal processing, and performance." Optics Express vol. 11, No. 7; Apr. 7, 2003; pp. 794-809.

Yang, V.X.D., N. Munce, J. Pekar, M.L. Gordon, S. Lo, N.E. Marcon, B.C. Wilson, and I.A. Vitkin, "Micromachined array tip for multifocus fiber-based optical coherence tomography." Optics Letters, 29, 1754-1756 (2004).

Yun, S.H., G.J. Tearney, J.F. de Boer, and B.E. Bouma. "Motion artifacts in optical coherence tomography with frequency-domain ranging." Optics Express vol. 12, No. 13; Jun. 28, 2004; pp. 2977-2998.

Yun, Seok H., Guillermo J. Tearney, Benjamin J. Vakoc, Milen Shishkov, Wang Y. Oh, Adrien E. Desjardins, Melissa J. Suter, Raymond C. Chan, John A. Evans, Ik-Kyung Jang, Norman S. Nishioka, Johannes F de Boer, and Brett E. Bouma. "Comprehensive volumetric optical microscopy in vivo" Nature Medicine, vol. 12, No. 12: Dec. 2006, pp. 1429-1433.

Zhang, Jun, and Zhongping Chen. "In vivo blood flow imaging by a swept laser source based Fourier domain optical Doppler tomography." Optics Express vol. 13, No. 19; Sep. 19, 2005; pp. 7449-7457.

Zipfel, W.R., Williams, R.M., Christie, R., Nikitin, A.Y., Hyman, B.T., and Webb, W.W., "Live tissue intrinsic emission microscopy using multiphoton-excited native fluorescence and second harmonic generation," PNAS Early Edition, www.pnas.org/cgi/doi/10.1073/pnas.0832308100, (2003).

\* cited by examiner

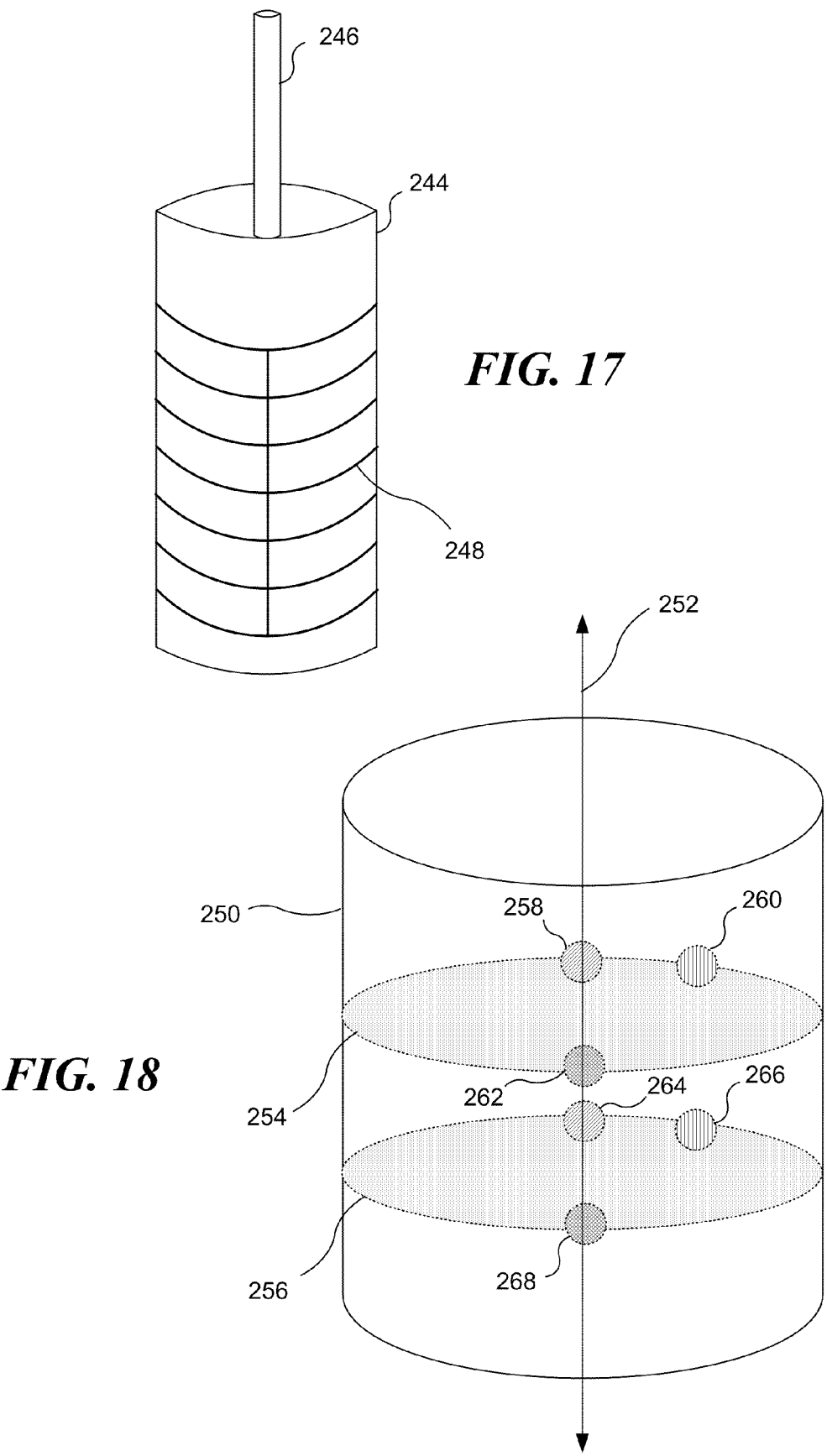

HIGH RESOLUTION OPTICAL COHERENCE TOMOGRAPHY BASED IMAGING FOR INTRALUMINAL AND INTERSTITIAL USE IMPLEMENTED WITH A REDUCED FORM FACTOR

RELATED APPLICATIONS

This application is based on a prior provisional application, Ser. No. 60/915,903, filed on May 3, 2007, the benefit of the filing date of which is hereby claimed under 35 U.S.C. §119 (e). This application is also a continuation-in-part of a co-pending U.S. patent application Ser. No. 10/880,008, filed on Jun. 28, 2004, the benefit of the filing date of which is hereby claimed under 35 U.S.C. §120.

GOVERNMENT RIGHTS

This invention was made with U.S. Government support under grant No. 1-R21-EB003284-01 awarded by the National Institutes of Health and grant No. BES-0348720 awarded by the National Science Foundation. The U.S. Government has certain rights in the invention.

BACKGROUND

Optical Coherence Tomography (OCT) is an emerging non-invasive biomedical imaging technology that can perform cross-sectional imaging of tissue microstructures in vivo and in real-time. OCT is analogous to ultrasound, except that it uses low coherence light, rather than acoustic waves. The echo delay time or the depth of light backscattered from tissue is measured using a technique referred to as low coherence interferometry.

OCT has significant advantages over other medical imaging technologies. Medical ultrasound, magnetic resonance imaging (MRI), and confocal microscopy are ill suited to high-resolution morphological deep tissue imaging, as ultrasound and MRI have insufficient resolution for imaging microstructures, while confocal microscopy lacks the ability to image deeply enough (i.e., beyond several hundred micrometers in highly scattering tissues), an ability that is required for morphological tissue imaging. OCT is analogous to ultrasound B-mode imaging, except that it uses low coherency, near-infrared light, rather than sound, and no matching medium is required. OCT imaging is non-invasive, and imaging can be performed in situ and in real time. In addition to micro-structural imaging, OCT can also provide additional functional information, such as high-resolution Doppler flow, and spatially revolved tissue spectroscopy.

As indicated above, a fundamental aspect of OCT is the use of low coherence interferometry (either in the time domain or the Fourier domain). In conventional laser interferometry, the interference of light occurs over a distance of meters. In OCT, the use of broadband light sources (i.e., light sources that can emit light over a broad range of frequencies) enables the interference to be generated within a distance of micrometers. Such broadband light sources include super luminescent diodes (i.e., super bright light emitting diodes (LEDs)), extremely short pulsed lasers (i.e., femto-second lasers) and wavelength/frequency-swept lasers. White light can also be used as a broadband source.

Essentially, the combination of backscattered light from the sample arm and reference light from the reference arm gives rise to an interference pattern, but only if light from both arms have traveled "substantially the same" optical distance (where "substantially the same" indicates a difference of less than a coherence length). By scanning the mirror in the reference arm or using Fourier domain techniques, a reflectivity profile of the sample can be obtained. Areas of the sample that reflect more light will create greater interference than areas that reflect less light. Any light that is outside the short coherence length will not contributes significantly to the interference signal. This reflectivity profile, referred to as an A-scan, contains information about the spatial dimensions and location of structures within the sample. An OCT image (i.e., a cross-sectional tomograph generally referred to as a B-scan), may be achieved by laterally combining multiple adjacent axial scans at different transverse positions.

FIG. 1 (Prior Art) schematically illustrates a conventional OCT system. This system includes a Michelson interferometer that uses a low coherence light source 20. The light source is coupled to an OCT probe 24 in the sample arm and to a reference arm 28 through an optical fiber coupler or beam splitter 22. The sample arm delivers an optical beam from the light source to a target 26 (generally a tissue sample) and collects the backscattered light. The reference arm provides a reference optical path length for the interference signal (with the path length scanned as in time-domain OCT or unscanned as in Fourier domain OCT). Path length scanning can be achieved, for example, by using a translating retro-reflective mirror or a phase-controlled scanning delay line (not separately shown). A backscattered intensity versus depth data set is developed with an axial scan. Two- or three-dimensional data sets formed by multiple adjacent axial scans are obtained by scanning the OCT beam along the transverse direction after each axial scan. A photodetector 30 (or a detector array) produces a corresponding analog signal comprising the data set. The analog signal is processed by detection electronics module 32, which produces corresponding digital data. The resulting digital data set can be further processed, displayed and stored, using a computer 38, as a false-color or gray-scale map, to form a cross-sectional OCT image. Barrett's esophagus is a chronic metaplastic condition characterized by a change in the epithelial lining of the esophagus, from normal squamous epithelium to a specialized columnar epithelium. Its prevalence is highly correlated to gastro esophageal reflux disease. Although Barrett's esophagus often does not cause symptoms, individuals having this condition have a significantly higher risk of developing esophageal cancer. The incidence of this usually lethal malignancy has increased 350% over the past two decades in the United States. Currently, the standard surveillance procedure for Barrett's epithelium is endoscopy, along with four-quadrant pinch biopsies at 1-2 cm intervals throughout the Barrett's epithelium. Recently, minimally invasive endoscopic ablative therapies (such as PDT, and electro or laser coagulation) have been developed and show significant potential to eradicate Barrett's esophagus, with the goal of preventing the development of esophageal cancer. Following ablation, there is return of normal-looking squamous epithelium. However, biopsy studies have shown that residual Barrett's esophagus remains underneath the neo-squamous epithelium in approximately 5% of cases. The true prevalence of this condition could be much higher, considering the random sampling nature of biopsy. Residual Barrett's epithelium under squamous epithelium has been reported to lead to the development of cancer. A major concern for ablative therapies is that if Barrett's remains under squamous epithelium, it cannot be detected using conventional endoscopic technologies. Currently, there are no imaging techniques that are capable of detecting islands of Barrett's epithelium under squamous epithelium. It would thus be desirable to provide a method and apparatus that can be used to detect such residual Barrett's epithelium.

Referring to FIG. 1, it will immediately be apparent that the form factor or size of OCT probe 24 limits the application of this technology within the body of a patient. However, reduced form factor OCT probes have been developed for use with intra-luminal, intravascular and interstitial catheters. FIG. 2A schematically illustrates a Prior Art catheter-based OCT probe 40, which includes a single mode optical fiber 44 for conveying light to and from a sample 52, a gradient index (GRIN) lens 46, and a beam deflecting element 48. These optical elements are disposed in a housing 42, and an opening 50 in housing 42 enables light to reach sample 52. In general, an object distance, L1, combined with properties of the lens, determines a working distance, W1, that can be achieved.

FIG. 2B (Prior Art) graphically illustrates the relationship between object distance, working distance, and transverse resolution that can be achieved using the probe configuration of FIG. 2A. At a working distance of about 8 mm (required for esophageal imaging), the best transverse resolution obtainable with a given GRIN lens using the probe configuration of FIG. 2A is about 75 microns, assuming that that the optical fiber and GRIN lens are coupled using optical cement (i.e., L1 corresponds to the thickness of the layer of optical cement). Unfortunately, that resolution is insufficient to enable fine structures (i.e., structures less than about 50 um in size) to be detected using OCT imaging. It would be desirable to provide additional probe designs facilitating improved resolution, while maintaining a compact form factor.

SUMMARY

A key aspect of the concepts disclosed herein relates to optical configurations enabling exemplary reduced form factor OCT probes to be achieved. As noted above, existing reduced form factor OCT probes do not have sufficient transverse resolution at a working distance of about 8 mm or larger (e.g. 12-15 mm) to enable Barrett's endothelium to be detected using OCT imaging. Disclosed herein are a plurality of optical configurations enabling reduced form factor OCT probes to be achieved, with increased transverse resolution, enabling such OCT probes to be employed to detect Barrett's endothelium using OCT imaging. The various configurations exhibit consistent performance parameters, permitting accurate prediction of their performance when used as an OCT probe, facilitating engineering various probes according to specific needs. As described in greater detail below, such reduced form factor OCT probes with enhanced transverse resolution can also be employed for other medical imaging purposes.

Significantly, where a relatively high resolution is desired, without also requiring a reduced form factor, larger aperture optics could simply be employed. In the context of the concepts disclosed herein, it will be understood that the OCT imaging probes will be employed in a body lumen or orifice or interstitially, so that such larger optics cannot be employed to achieve the desired resolution, because of the form factor limitations imposed by anatomical restrictions. Preferably, OCT probes for use in body lumens will be about 3 mm in diameter or less, with OCT probes designed for use interstitially will be about 500 um in diameter or less. To achieve the required form factor and resolution, compound optics are employed.

In an exemplary embodiment, the compound optics include a beam adjusting element configured to manipulate light from the optical fiber so that a light beam exiting a distal end of the beam adjusting element has a smaller beam diameter than a light beam exiting the distal end of the optical fiber, thus increasing a numerical aperture of the OCT probe relative to that at the distal end of the optical fiber, and a distal lens element configured to focus light manipulated by the beam adjusting element at the predefined working distance proximate the sample. In particularly preferred embodiments, the beam adjusting element and distal lens element are implemented using GRIN lenses.

Thus, one aspect of the concepts disclosed herein is an OCT imaging probe including a single mode optical fiber and a compound lens for focusing light from the single mode optical fiber at a predefined working distance, while enabling a diameter of the optical probe to be reduced as compared to an optical probe configured to focus light at the predefined working distance using a single component lens. In at least one embodiment, the compound lens is configured such that a position of individual elements in the compound lens are fixed relative to one another. Preferably, the compound lens comprises a plurality of GRIN lenses or other miniature lenses (preferably with a cylindrical shape to facilitate probe manufacturing). The optical properties of the plurality of GRIN lenses are selected to achieve a desired resolution. If side scanning or circumferential scanning is desired, a beam reflecting element can be disposed distally of the compound lens. If forward scanning is desired, no beam reflecting element is required. With respect to esophageal imaging in particular, side scanning/circumferential scanning is particularly preferred. In embodiments where two different GRIN lenses are employed, the GRIN lenses can, for example, be adhesively coupled together using optical cement. In some embodiments, an optically transparent element is disposed between the proximal GRIN lens and the single mode optical fiber. Significantly, a length of the optically transparent element corresponds to an object distance, a linear dimension of which has an effect on the transverse resolution that can be achieved using the selected GRIN lenses. The linear dimension of the optically transparent element required to provide the desired resolution is calculated (based on the optical properties of the selected GRIN lenses and a predetermined working distance), and the optically transparent element is cleaved to achieve the required dimension. The optically transparent element is then thermally fused to a distal end of the single mode optical fiber and to a proximal end of the most proximally disposed GRIN lens. The use of the thermally fusing technique is significant. If optical cement were used for joining the optically transparent element to the single mode optical fiber and to the GRIN lens, that optical cement would have a specific linear dimension, which in turn would affect the transverse resolution (by effecting the object distance) that could be achieved using a particular combination of lenses and a specific working distance. It is very difficult to control a shape of a layer of optical cement joining two optical components, and the relative positions of the two optical components to be connected, when the gap between the optical components to be connected is relatively large (e.g. larger than a diameter of the larger of the two optical components). A relatively long junction made of optical cement could compromise the mechanical robustness of the probe. Thus, in the context of a high resolution and robust OCT imaging probe, the use of optical cement in a location corresponding to a relatively large object distance is undesirable (e.g. larger than a diameter of the larger of the two optical components). The thermal fusion technique enables the object distance to be more precisely controlled, which in turn enables the working distance and transverse resolution to be more precisely calculated and implemented. In addition, junctions made by thermal fusion have proven to be mechanically robust. Preferably, the optically transparent element is a glass rod, whose diameter substantially corresponds to a diameter of the single mode optical fiber. Note that the dimension of the optically transparent element is chosen to ensure no beam clipping occurs within the optically transparent element, and the beam diameter can be predicted when the distal and proximal GRIN lenses and the object distances are determined, to achieve a desired transverse resolution at a given working distance.

In embodiments employing two different GRIN lenses, the GRIN lenses can be selected such that a proximal GRIN lens is configured to increase a numerical aperture of the OCT probe relative to the distal end of the single mode optical fiber and to reduce the beam mode-field diameter from the single mode fiber to a smaller diameter at an exit surface of the proximal GRIN lens, and the distal GRIN lens is configured to focus light from the OCT probe at the predefined working distance.

In exemplary embodiments employing three different GRIN lenses, a first GRIN lens is thermally fused to a distal end of the single mode optical fiber. The first GRIN lens is then thermally fused to a second GRIN lens, and the second GRIN lens is adhesively coupled to a third GRIN lens. Generally, consistent with the linear dimension of the optically transparent element discussed above, a linear dimension of the first GRIN lens can be precisely controlled to achieve a desired resolution based on the optical properties of the GRIN lenses and a predefined working distance. Again, the required linear dimensions (for the first and second GRIN lens, which are preferably the same diameter as the single mode fiber) take into account that no beam clipping occurs within the two GRIN lenses, the beam spot size at the exit surface of the second GRIN lens is minimized, and the gap between the second and the third GRIN lenses is relatively small (such that the gap can be filled using optical cement).

In exemplary embodiments employing three different GRIN lenses, the GRIN lenses are selected such that a proximal GRIN lens is configured to collimate light emitted from the distal end of the single mode optical fiber, a middle GRIN lens is configured to receive the collimated light and to refocus the beam with an increased numerical aperture relative to the distal end of the single mode optical fiber, and a distal GRIN lens is configured to focus light from the middle GRIN lens at the predefined working distance. A diameter of the proximal and middle GRIN lenses can be substantially the same as a diameter of the single mode optical fiber and substantially smaller than a diameter of the distal GRIN lens, greatly facilitating the manufacturing process.

Where the optical probe is intended to be used for esophageal imaging, the predefined working distance can range from about 8 mm to about 15 mm. A working distance of 8 mm was selected to serve as an example for analysis and illustration. One exemplary embodiment of the OCT probe further comprises an inflatable balloon configured to center the OCT probe in the esophagus, and to substantially flatten esophageal folds.

Another aspect of the concepts disclosed herein is a system for high-resolution OCT imaging of the esophagus. One exemplary embodiment of such a system comprises a low coherence light source, a sample arm having an OCT probe that includes a single mode optical fiber and a compound lens and which is configured to scan an esophagus. The embodiment also includes a reference arm, a detector, a prime mover (such as an electric motor), and a fiber-optic rotary joint disposed at a proximal end of the OCT probe. The rotary joint cooperates with the prime mover to enable the OCT imaging probe to be selectively rotated within the balloon catheter, and with a linear translation component to enables the OCT probe to be selectively linearly translated within the balloon catheter relative to the esophagus. A processor and memory are logically coupled to the detector, the OCT probe, the prime mover, and the translation component. The processor is configured to execute a plurality of machine instructions residing in the memory to carry at least one of circumferential scanning of an esophagus, and three-dimensional spiral imaging of the esophagus.

Another aspect of the concepts disclosed herein is directed to an optical probe for use in high resolution OCT imaging. An exemplary embodiment of the optical probe includes a single mode optical fiber and a beam focusing structure. The beam focusing structure has a plurality of optical elements, including at least one GRIN lens; a proximal element in the beam focusing structure is thermally fused to a distal end of the single mode optical fiber.

Another aspect of the concepts disclosed herein is a method for detecting under (or sub-) squamous Barrett's endothelium using OCT imaging. In the method, a medical device that includes an OCT probe in an expandable member is introduced into a patient's esophagus. The OCT probe is configured to detect not only visible Barrett's endothelium at the surface of the esophageal wall, but also Barrett's tissue hidden under normal-looking squamous epithelium (referred to as sub-squamous Barrett's epithelia or glands). The expandable member is employed to center the OCT probe in the patient's esophagus and to substantially flatten esophageal folds. The OCT probe is activated, and the medical device is manipulated to achieve at least one of circumferential OCT imaging and three-dimensional spiral OCT imaging, thereby collecting OCT image data. The OCT image data is then analyzed to detect the presence of Barrett's endothelium, if present in the patient's esophagus.

Another aspect of the concepts disclosed herein is an optical probe for use in high resolution OCT guided needle biopsy. An exemplary optical probe includes a needle-like housing, a single mode optical fiber, and an optical element for focusing light from the single mode optical fiber to the predefined working distance. A proximal end of the optical element is thermally fused to a distal end of the single mode optical fiber, and a length of the optical element is determined as a function of the predefined working distance. The optical element can be a GRIN lens, in at least one exemplary embodiment. In some exemplary embodiments, the optical element and a distal end of the single mode optical fiber are disposed in a durable glass inner housing, which is disposed within the needle-like housing. In other exemplary embodiments, the optical element is a compound lens, comprising two or three GRIN lenses, oriented generally consistent with the configurations discussed above.

Still another aspect of the concepts disclosed herein is a method for making an optical probe for use in high resolution OCT imaging. This method includes the step of selecting a working distance for which the optical probe will be optimized. A single mode optical fiber, a first optical element, and a second optical element selected as a function of the working distance are provided. A distal end of the first optical element is fixedly coupled with the second optical element using optical cement. Based on a first linear dimension of the combined first and second optical elements, a second linear dimension of the first optical element required to enable the selected working distance to be achieved is then determined. The first optical element is sized so as to achieve the second linear dimension, and a proximal end of the first optical element is thermally fused to a distal end of the single mode optical fiber and to a proximal end of the second optical element, such that the first optical element is disposed between the single mode optical fiber and the second optical element. In some related exemplary embodiments, the first optical element is a glass rod to expand the beam diameter as it is conveyed to the next optical element; while in other exemplary embodiments, the first optical element is a GRIN rod lens configured to similarly expand the beam diameter, collimate light from the single mode optical fiber, and direct the collimated light to the next optical element. The second optical element can be a compound lens comprising two GRIN lenses, which are coupled together. Preferably all the optical elements, including the single mode fiber, the glass rod, the first GRIN (rod) lens, and the final GRIN lens are thermally fused together, to provide enhanced mechanical stability and to facilitate manufacture. However, particularly if the final GRIN lens has a diameter that differs from a diameter of the preceding optical element, that optical element and the last GRIN lens can be coupled together with optical cement.

If desired, a matching fluid can be introduced into any voids within the probe housing of any of the exemplary OCT probes described above. Furthermore, additional elements can be incorporated to facilitate variable focus and focus tracking. Such elements are described in detail in a commonly assigned U.S. patent application Ser. No. 11/332,780, entitled "Simultaneous Beam Focus and Coherence Gate Tracking for Real-Time Optical Coherence Tomography," the specification and disclosure of which are hereby specifically incorporated herein by reference.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 2A:
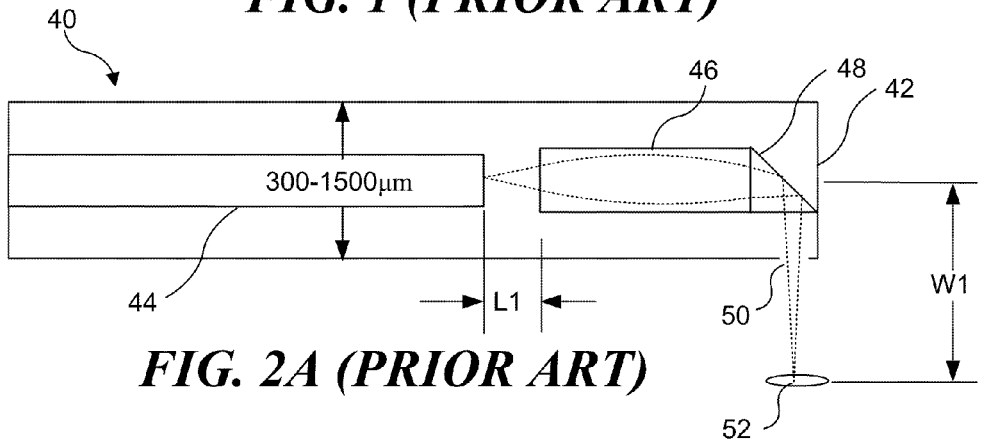
FIG. 2A (Prior Art) is a schematic representation of a prior art OCT probe having a relatively small form factor suitable for use in a catheter.
Figure 2B:
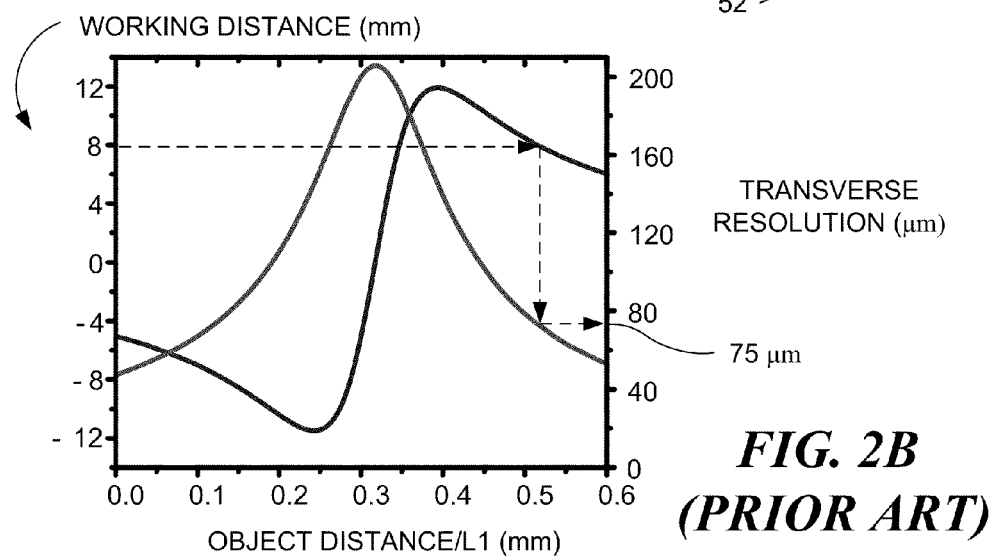
Figure 3A:
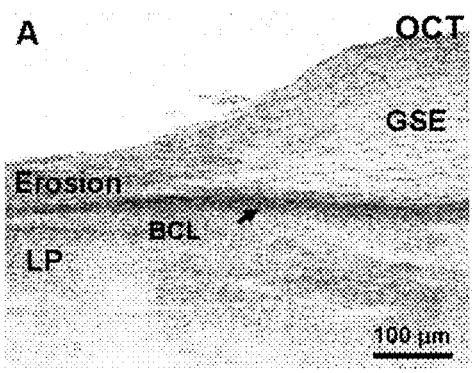
Figure 3B:
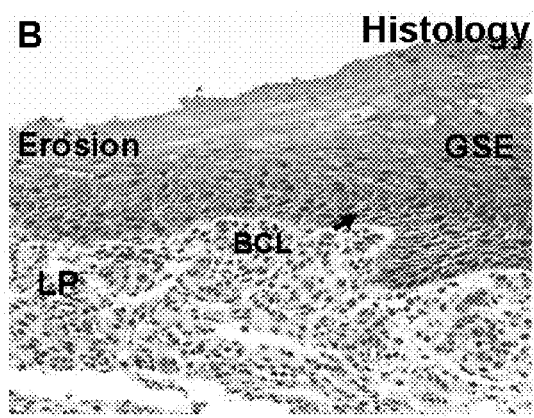
Figure 3C:
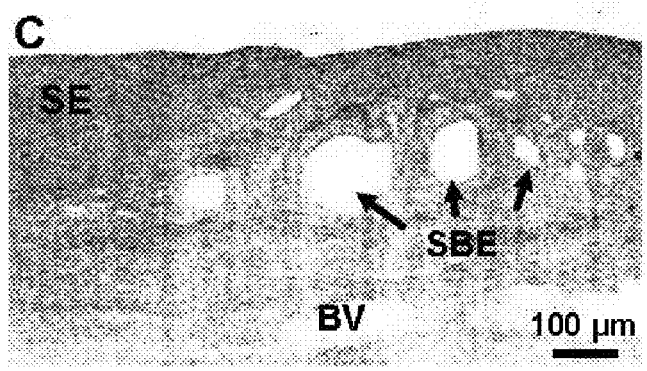
Figure 3D:
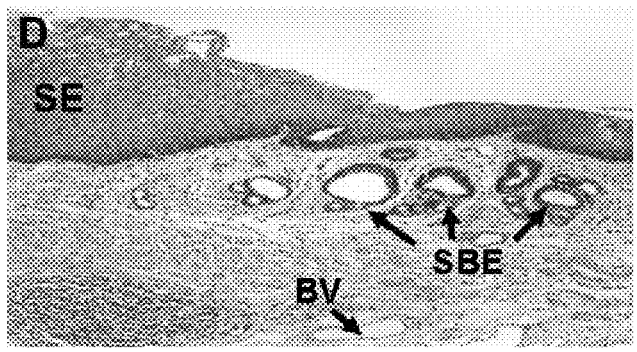
Figure 4:
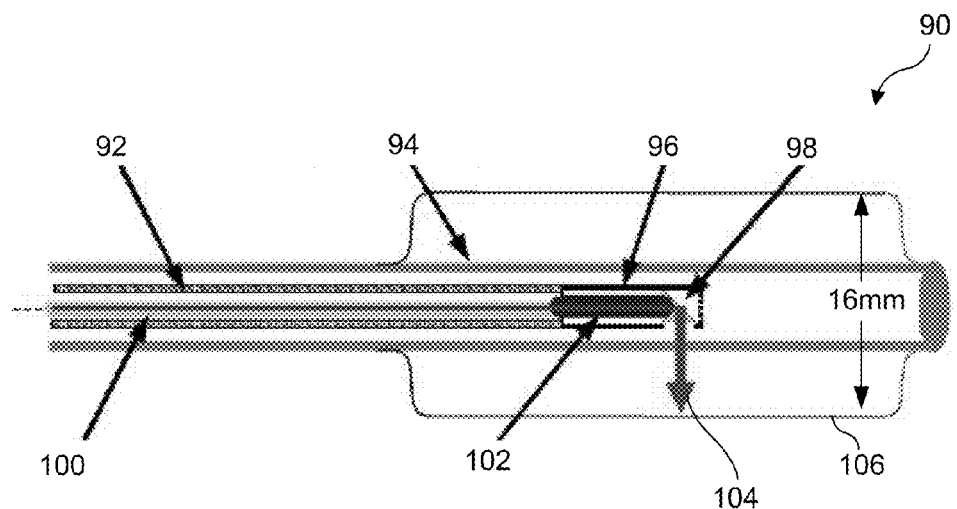
Figure 5A:
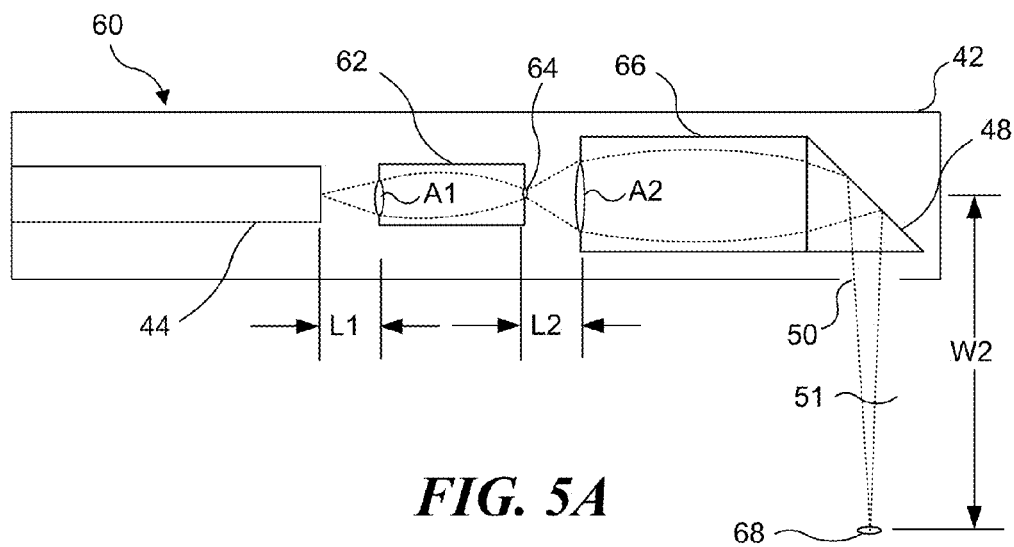
Figure 5B:
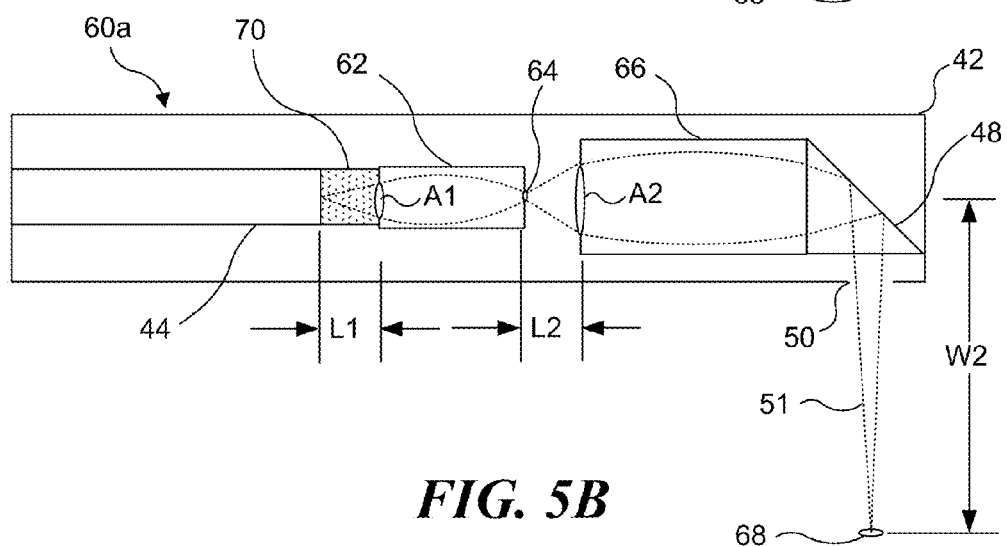
Figure 5C:
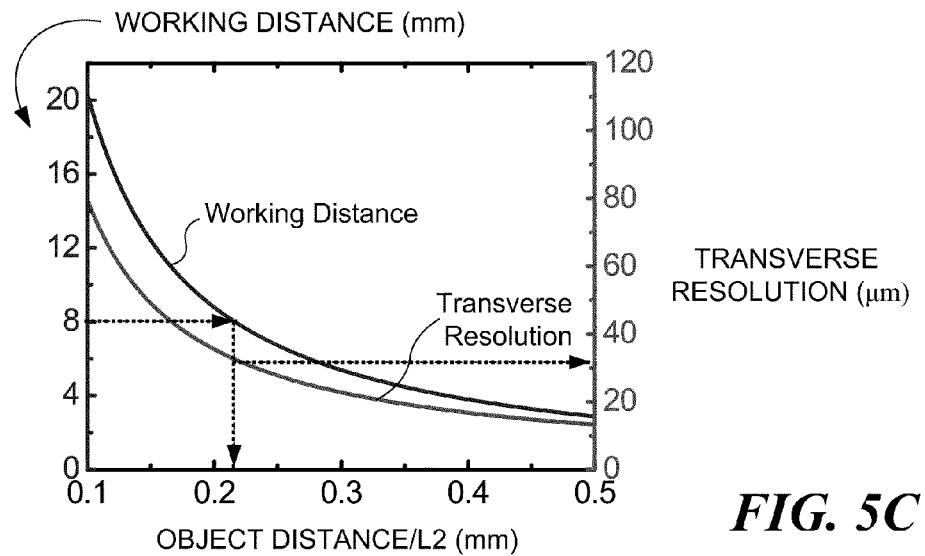
Figure 5D:
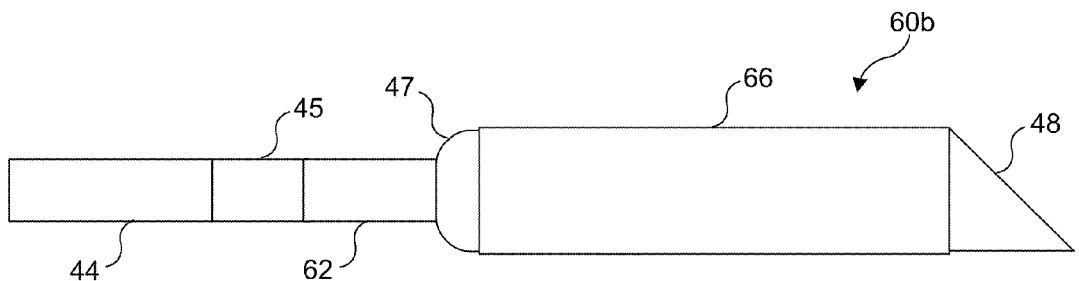
Figure 5E:
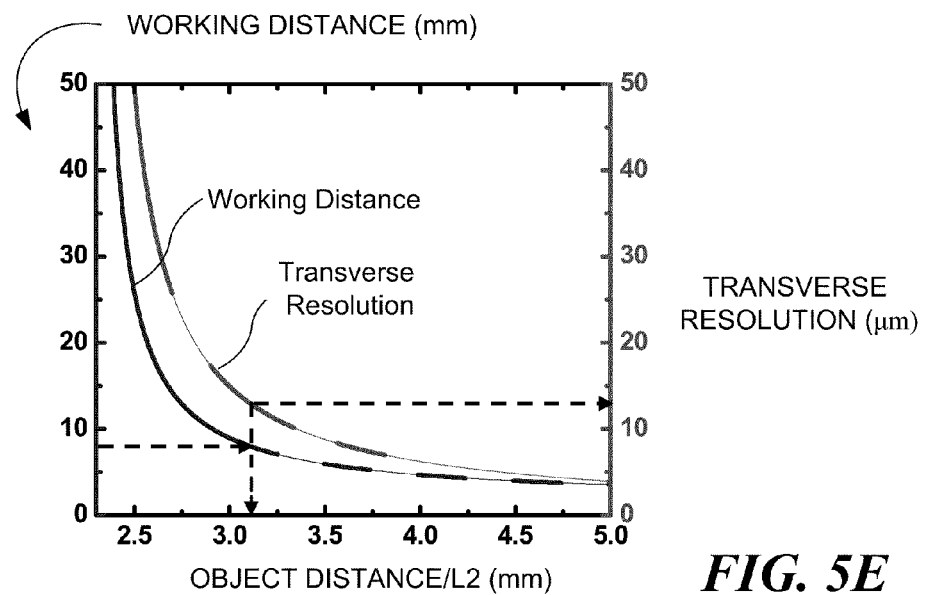
Figure 5F:
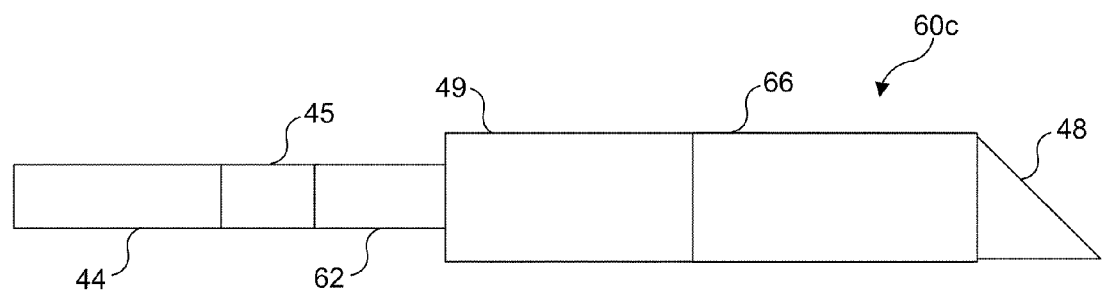
Figure 6:
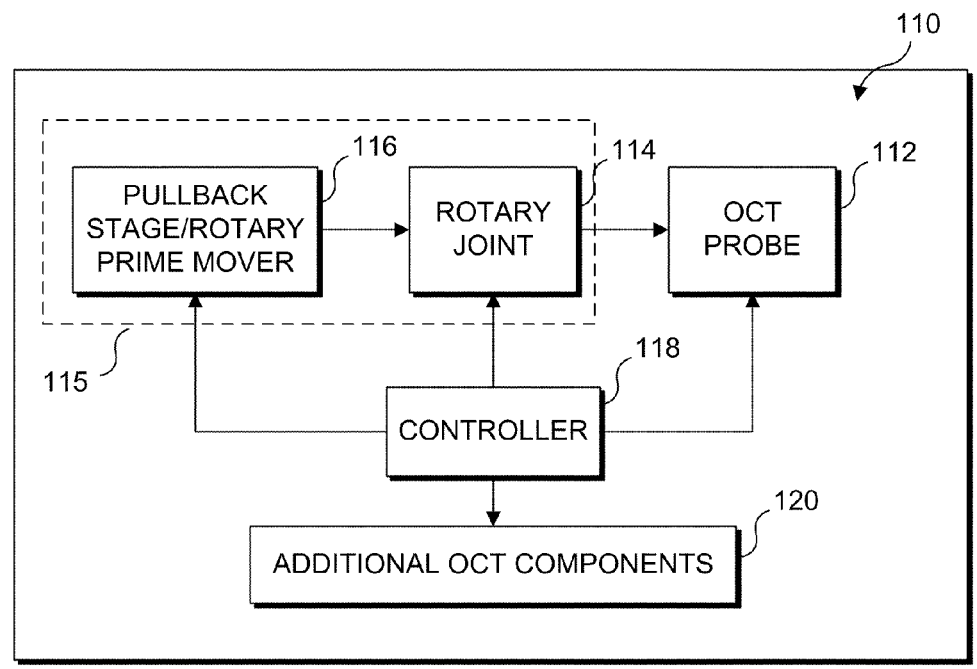
Figure 7A:
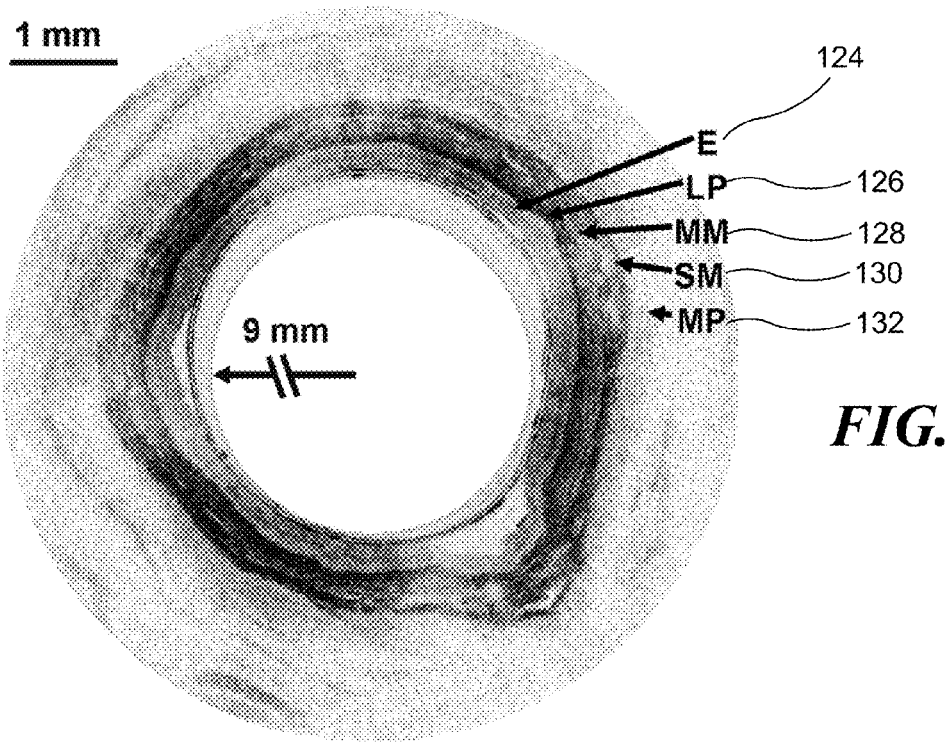
Figure 7B:
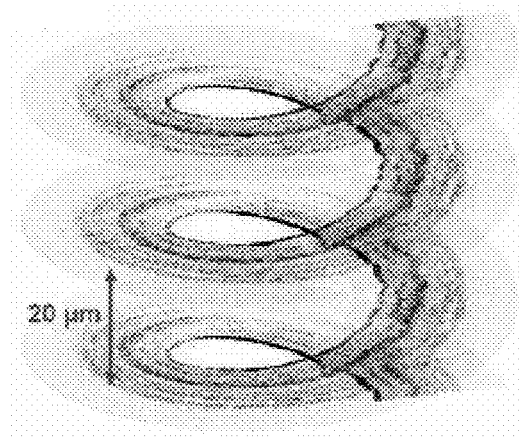
Figure 8:
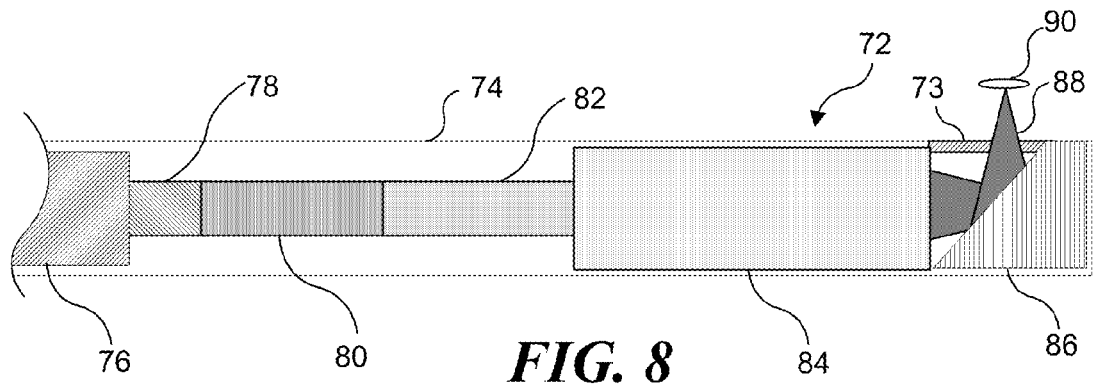
Figure 9:
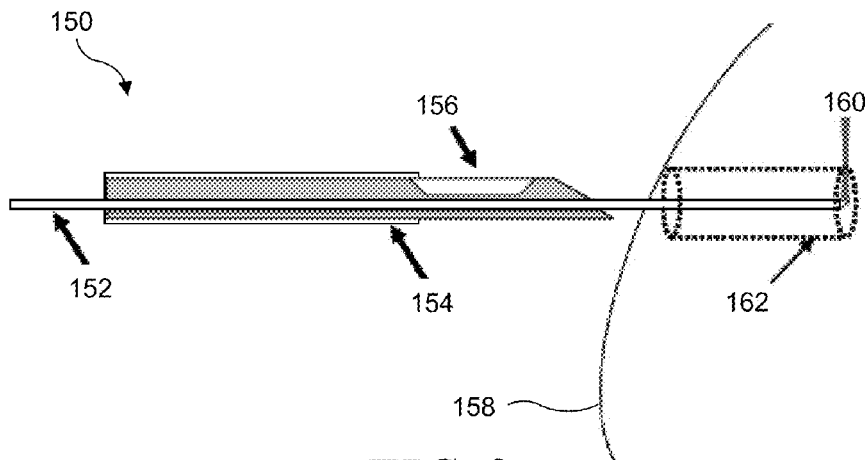
Figure 10A:
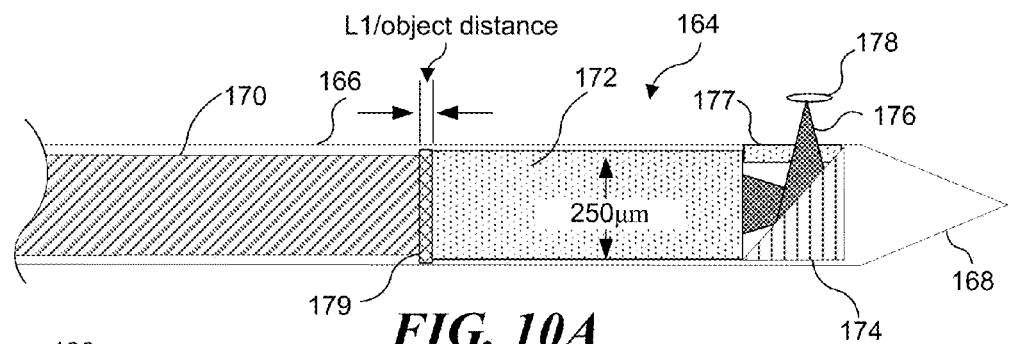
Figure 10B:
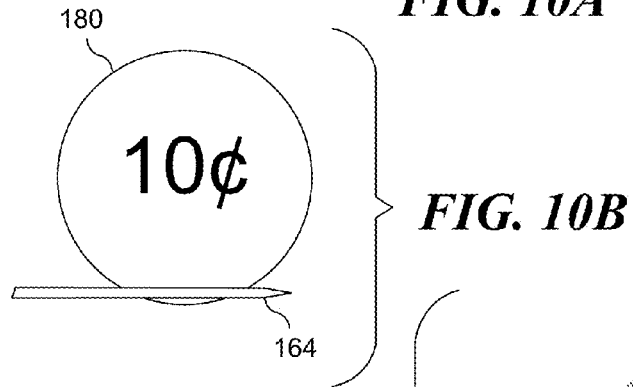
Figure 10C:
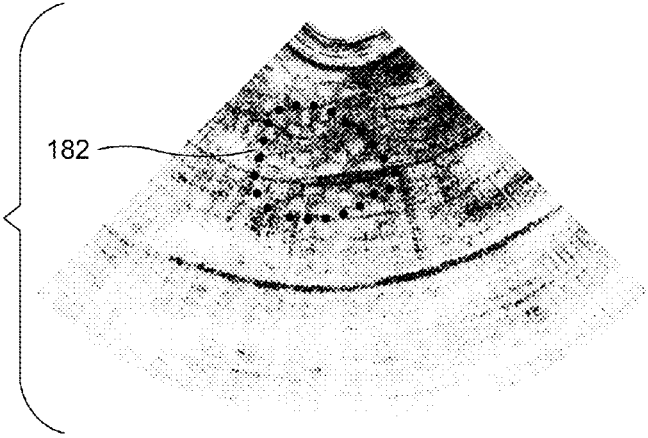
Figure 10D:
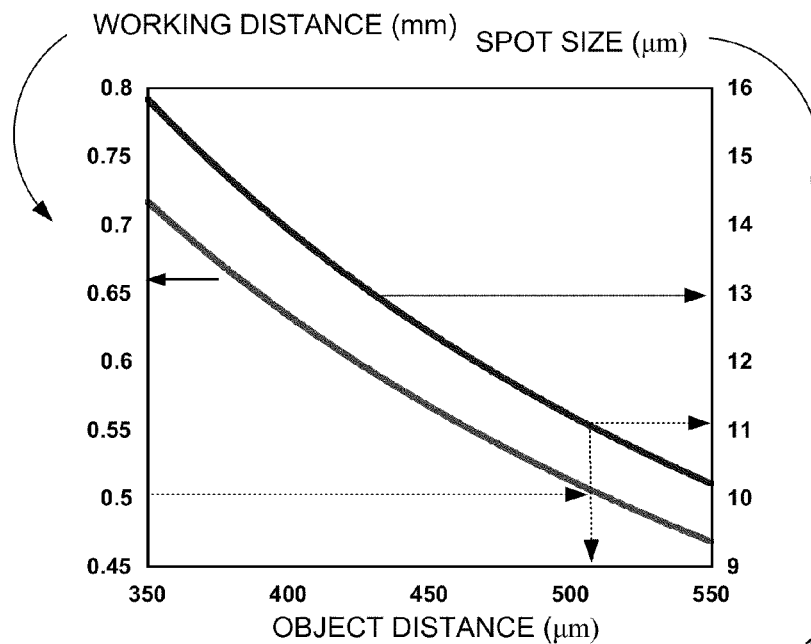
Figure 11:
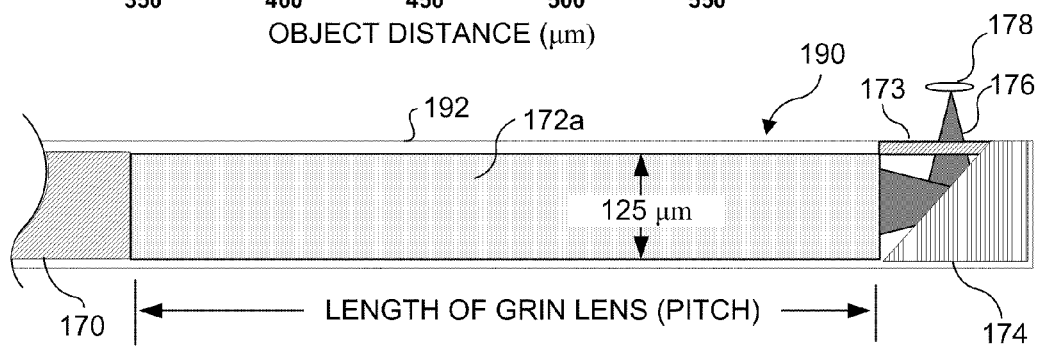
Figure 12:
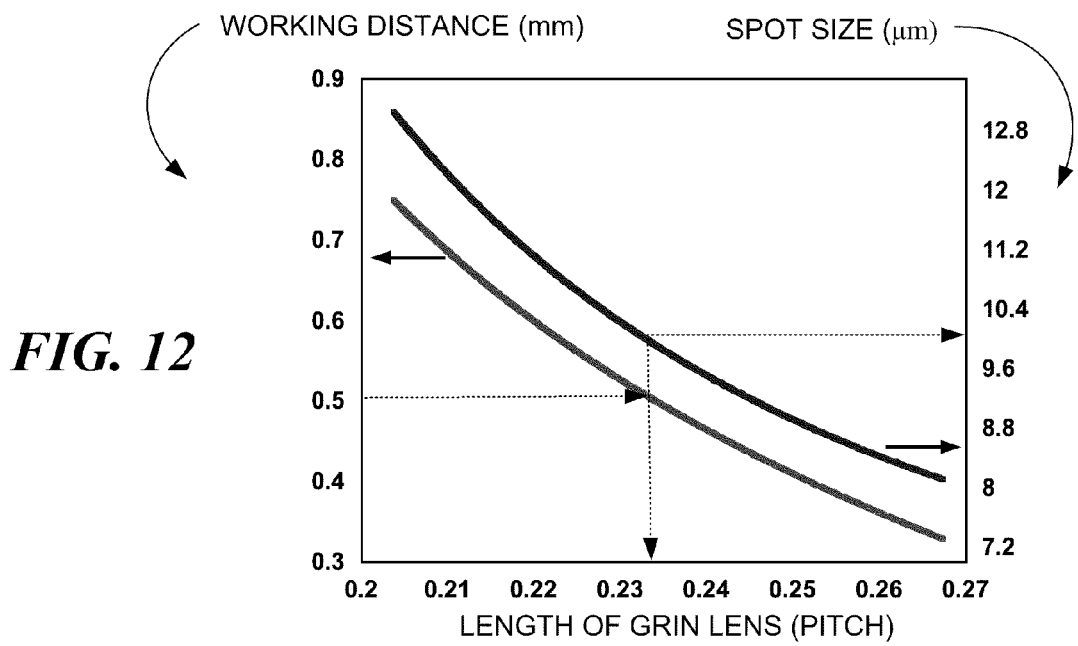
Figure 13:
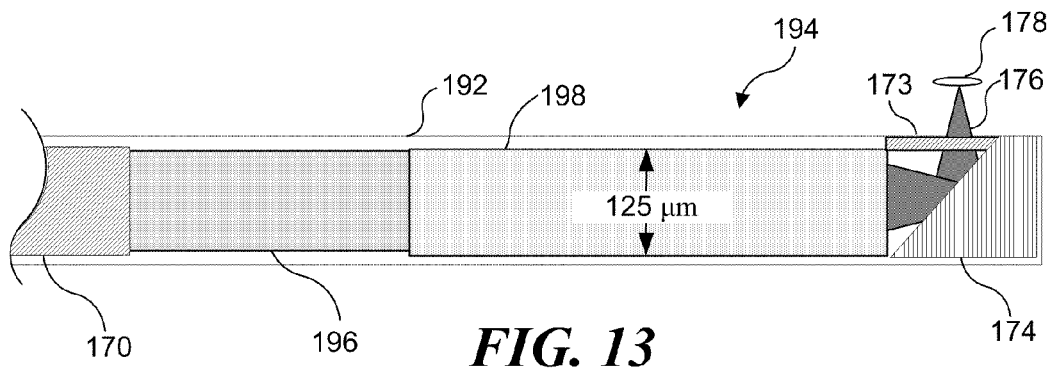
Figure 14:
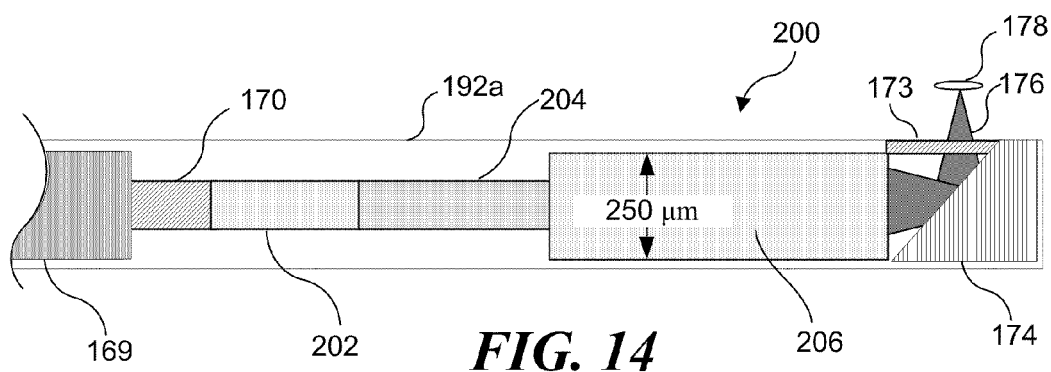
Figure 15A:
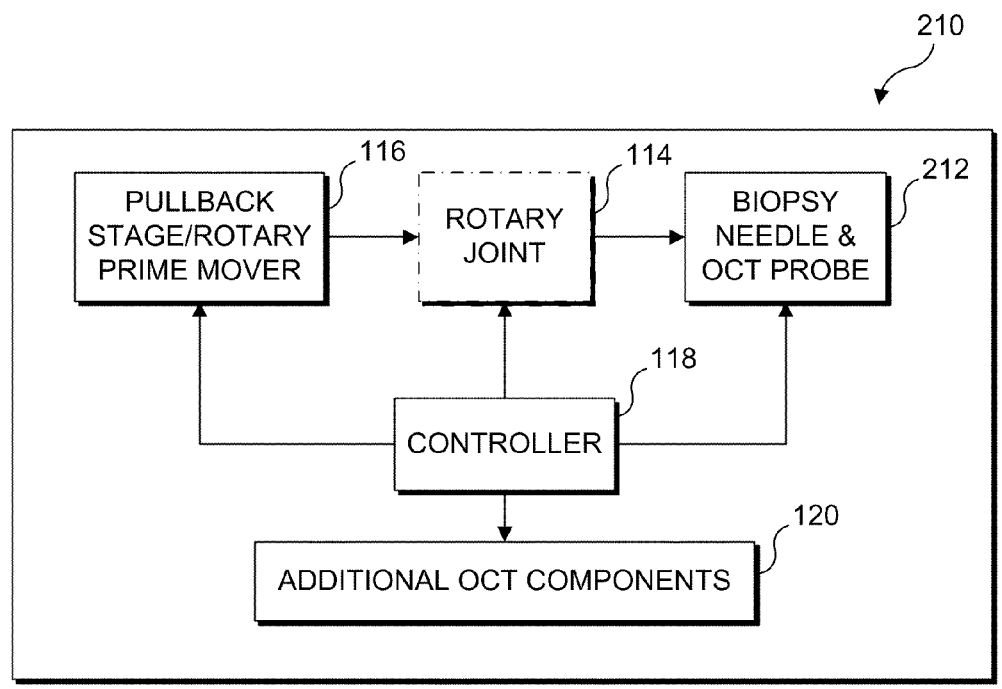
Figure 15B:
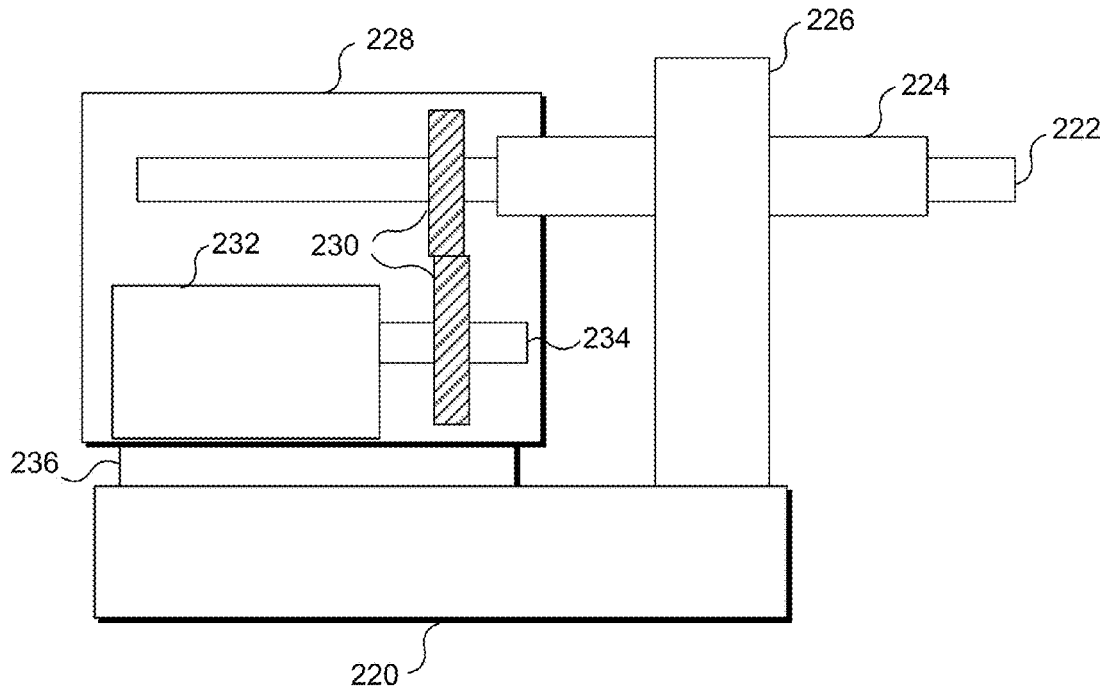
Figure 16:
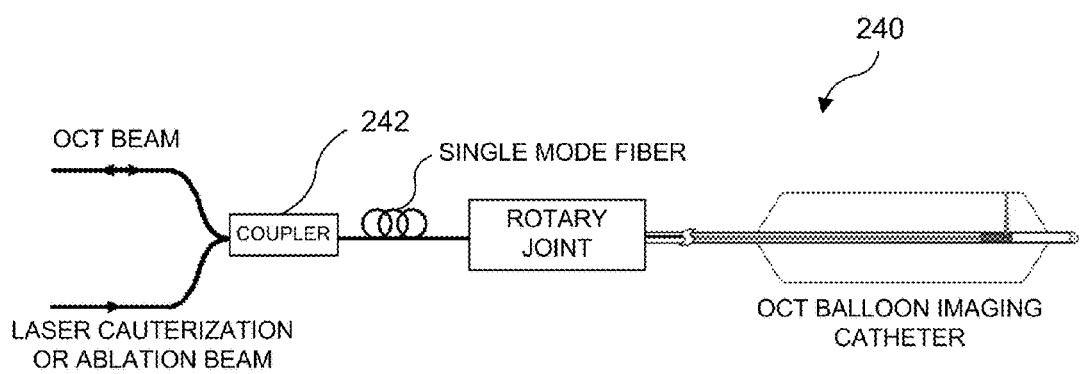

FIG. 2B (Prior Art) graphically illustrates the relationship between working distance, object distance, and transverse resolution that can be achieved using the OCT probe of FIG. 2A;

FIG. 3A is an OCT image including the features of glycogenic squamous endothelium (GSE), an ulcer, a basal cell layer (BCL), and lamina propria (LP);

FIG. 3B is a conventional histological image of the same portion of tissue shown in FIG. 3A, including the features of glycogenic squamous endothelium, an ulcer, the basal cell layer (BCL), and the lamina propria (LP), confirming that such features can be clearly visualized in OCT images;

FIG. 3C is an OCT image including the features of squamous epithelium (SE), sub-squamous Barrett's epithelia (SBE) or glands, and blood vessels (BV);

FIG. 3D is a conventional histological image of the same portion of tissue shown in FIG. 3C, including the features of squamous epithelium (SE), sub-squamous Barrett's epithelia (SBE) or glands, and blood vessels (BV), confirming that such features can be clearly visualized in OCT images;

FIG. 4 schematically illustrates an OCT probe combined with a balloon catheter, to enable esophageal OCT imaging to be used to detect Barrett's esophagus;

FIG. 5A schematically illustrates an OCT probe having a reduced form factor suitable for use in a catheter that employs a compound lens in order to increase a transverse resolution without increasing a relative size of the form factor, as compared to the prior art OCT probe of FIG. 2A;

FIG. 5B schematically illustrates an OCT probe similar to that illustrated in FIG. 5A, in which an optically transparent member is fused to a distal end of a single mode optical fiber and a proximal end of a first lens element, a linear dimension of the optically transparent member enabling a dimension of a first object distance L1 to be precisely controlled and the probe to be mechanically robust;

FIG. 5C graphically illustrates the relationship between working distance (W), object distance (L2), and transverse resolution that can be achieved using the OCT probe of FIG. 5B, which employs first and second GRIN lenses;

FIG. 5D schematically illustrates another OCT probe based on the probe of FIG. 5A, in which both a first object distance L1 and second object distance L2 can be precisely controlled;

FIG. 5E graphically illustrates the relationship between working distance, object distance L2, and transverse resolution that can be achieved using the OCT probe of FIG. 5B with a second GRIN lens having a shorter pitch length as compared with the second GRIN lens for the relationship of FIG. 5C (note the dramatic differences in object distance L2 for a working distance of 8 mm in FIGS. 5C and 5E);

FIG. 5F schematically illustrates yet another OCT probe based on the probe of FIG. 5D, in which both a first object distance L1 and second object distance L2 are precisely controlled by selecting a second GRIN lens having shorter pitch length as compared with the second GRIN lens for the relationship of FIG. 5C;

FIG. 6 is a functional block diagram of an OCT system incorporating the OCT probe of FIG. 5B, to enable esophageal OCT imaging to be used to detect Barrett's esophagus;

FIG. 7A is an esophageal OCT image acquired using a system substantially identical to that illustrated in FIG. 6, illustrating that circumferential esophageal OCT imaging is achievable;

FIG. 7B is an esophageal OCT image acquired using a system substantially identical to that illustrated in FIG. 6, illustrating that three-dimensional spiral esophageal OCT imaging is achievable;

FIG. 8 schematically illustrates an OCT probe including a compound lens formed from three GRIN lenses;

FIG. 9 schematically illustrates an OCT probe configured for image guided needle biopsy;

FIG. 10A schematically illustrates an OCT probe incorporated into a stainless steel hypodermic needle;

FIG. 10B schematically illustrates the relative sizes of the OCT probe of FIG. 10A and a U.S. 10 cent coin (i.e., a dime);

FIG. 10C is an OCT image including muscle fiber bundles obtained using the OCT probe of FIG. 10A, graphically illustrating that relatively small structures can be visualized in OCT images acquired using the OCT probe of FIG. 10A;

FIG. 10D graphically illustrates the relationship between working distance, object distance, and transverse resolution that can be achieved using the OCT probe of FIG. 10A;

FIG. 11 schematically illustrates an OCT probe incorporated into a transparent inner housing, the inner housing being small enough to be inserted into a stainless steel hypodermic needle;

FIG. 12 graphically illustrates the relationship between working distance, lens pitch, and transverse resolution that can be achieved using the OCT probe of FIG. 11;

FIG. 13 schematically illustrates an OCT probe incorporated into a transparent inner housing, the inner housing being small enough to be inserted into a stainless steel hypodermic needle, in which the OCT probe includes an optically transparent spacer between a distal end of a single mode optical fiber and a proximal end of a GRIN lens, the spacer enabling a desired resolution to be achieved at a given working distance;

FIG. 14 schematically illustrates an OCT probe incorporated into a transparent inner housing, the inner housing being small enough to be inserted into a stainless steel hypodermic needle, in which the OCT probe includes a compound lens including three different GRIN lens, the compound lens enabling a desired resolution to be achieved at a given working distance;

FIG. 15A is a functional block diagram of an OCT system incorporating one or more of the exemplary OCT probes of FIGS. 10A, 11, 13, and 14, to enable OCT image guided needle biopsy; and FIG. 15B schematically illustrates an exemplary OCT system incorporating one or more of the exemplary OCT probes of FIGS. 10A, 11, 13, and 14, to enable OCT image guided needle biopsy;

FIG. 16 is a functional block diagram of an OCT system incorporating a laser for marking a region of interest, where the laser light is delivered using the same optical fiber that is used for OCT imaging;

FIG. 17 schematically illustrates an exemplary OCT balloon catheter including electrodes on an outer surface of the balloon enabling marking to be implemented using electrocauterization; and FIG. 18 schematically illustrates a lumen marked using ink dots.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

Figure 1:
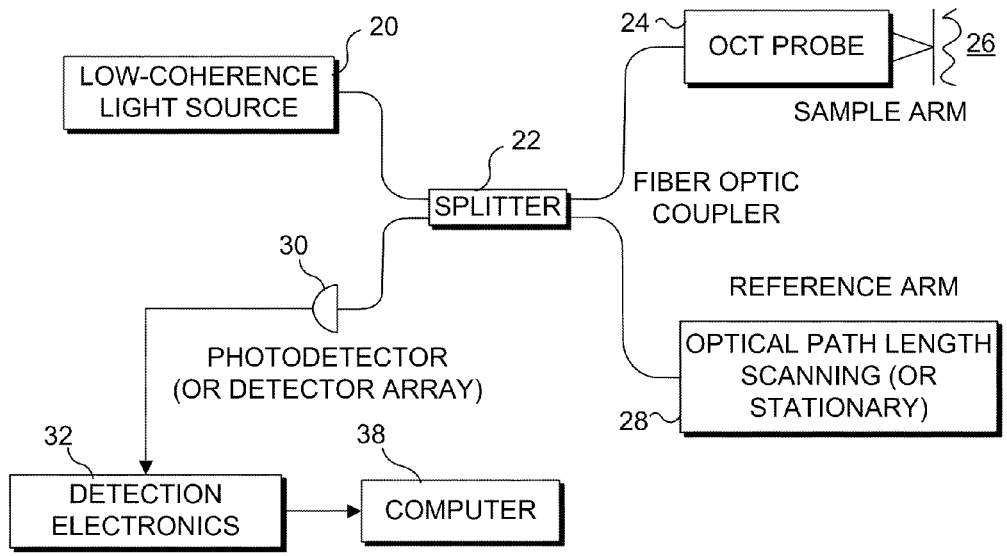
FIG. 1 (Prior Art) is a schematic block diagram of a typical OCT system.

Preliminary Ex-vivo Studies: One application of the concepts disclosed herein is to use OCT imaging to detect sub-squamous Barrett's esophagus (and other sub-squamous abnormal structures such as cancer). To determine whether OCT can be used to detect sub-squamous Barrett's esophagus, extensive ex vivo studies were performed. Fourteen human esophagectomy specimens were imaged using a bench-top OCT system (generally consistent with the OCT system illustrated in FIG. 1) with the esophageal specimen cut open. Representative OCT images are shown in FIGS. 3A and 3C, with FIGS. 3B and 3D showing corresponding histological images obtained using microscopic techniques. Features that can be identified in the OCT image of FIG. 3A and the corresponding histological image include normal glycogenic squamous epithelium (GSE), an ulcer (erosion), a basal cell layer (BCL), and lamina propria (LP). Significantly, such features are readily apparent in both the OCT image of FIG. 3A, as well as the corresponding histological image of FIG. 3B, indicating that such features can be readily identified in OCT images. Features that can be identified in the OCT image of FIG. 3C include sub-squamous Barrett's epithelium (SBE) and some blood vessels (BV). Significantly, such features are readily apparent in both the OCT image of FIG. 3C as well as the corresponding histological image of FIG. 3D, thus indicating that sub-squamous Barrett's glands (and some blood vessels) can be clearly identified in OCT images and correlate very well with histology.

A double-blind study has indicated that OCT imaging offers a more than 80% sensitivity and 90% specificity for detecting sub-squamous Barrett's esophagus. The main reason for a false positive diagnosis is the difficulty in distinguishing sub-squamous Barrett's glands from large blood vessels; however, this would not be a problem in an in vivo environment, because in vivo blood flow will enable blood vessels to be differentiated from sub-squamous Barrett's esophagus (i.e., in vivo Doppler imaging will enable blood vessels to be differentiated from Barrett's glands, as there will be no blood flow in the Barrett's structures).

Need for a Balloon Catheter: OCT imaging of internal organs (such as the gastrointestinal tract) has been made possible by the development of flexible and miniature fiber-optic OCT catheters, such as the OCT probe of FIG. 2A. The small diameter (1-2.5 mm) of an OCT catheter permits its delivery through the working channel (3.7 mm in diameter) of a standard GI endoscope. The procedure is to choose a region of interest under the field of view of a GI endoscope, deliver the OCT catheter to the region, and acquire high-resolution images in situ. In spite of two possible scanning modes (linear scan and circumferential scan), it is challenging for OCT imaging to be performed over a large area in a systematic fashion using current OCT catheters.

In the case of esophageal imaging, the esophagus folds present further challenges. In addition, imaging of a relatively large area requires a relatively prolonged imaging time, and consequently potential motion artifacts can be introduced into the images. Thus, in order to systematically image the esophagus over a large area, it will typically be necessary to stabilize the OCT catheter in relation to the esophagus, and to avoid the esophageal folding, so that imaging of the full circumference of the esophagus is possible. Thus, in one exemplary embodiment of the approach discussed herein, an OCT balloon catheter is used that integrates circumferential OCT imaging and position stabilization.

Such an exemplary OCT balloon catheter 90 is schematically illustrated in FIG. 4. In balloon catheter 90, an OCT probe is introduced into an inner lumen 94 of the catheter, and an additional lumen (not specifically shown) enables pressurized air (or some other fluid) to be supplied to inflate a balloon 106 that is included on the catheter. At least the portion of lumen 94 overlapping balloon 106 can be made of a generally optically transparent material, to enable a light beam 104 emitted from OCT optics 102 (and deflected by a reflector 98, which can comprise a micro prism) to reach a sample. Of course, at least a portion (or all) of balloon 106 is similarly optically transparent, for the same reason. Additional elements of the OCT probe include a single mode optical fiber 100, disposed within a hollow metal drive wire 92, which enables the OCT probe to be selectively positioned within lumen 94. OCT optics 102 can be enclosed in a durable housing 96 (such as a metal or glass housing), which includes an opening or transparent window adjacent to reflector 98 to enable light to reach a sample area.

The function of the balloon is to flatten out or generally reduce the esophageal folds and stabilize the OCT catheter. The radius of the balloon required to perform this function is about 8-15 mm (when inflated), which is approximately the radius of a human esophagus when the esophageal folds are flattened. Consequently, a relatively large working distance (i.e., ~8-15 mm) is required for the OCT catheter, which imposes a significant challenge in creating a usable optical design that can: (1) provide a reasonably useful transverse resolution; and, (2) maintain a small catheter diameter (e.g., 2 mm or less), so that the entire balloon catheter can still be delivered to the esophagus through the working channel of a GI endoscope. Significantly, most existing OCT imaging catheters require either direct or close contact with the esophageal wall, due to a relatively small 2-3 mm working distance. Thus, yet another aspect of the concepts disclosed herein is an optical design that achieves a high transverse resolution (~20-40 µm) in a compact form factor (i.e., having a diameter that is less than or equal to about 1.5 mm), with a working distance sufficient for enabling the OCT optics to be spaced apart from the esophageal wall to achieve the circumferential imaging noted above. Effective parameters for such an optical design include a target transverse resolution of approximately 20-40 µm, a working distance of approximately 8-15 mm, and an overall optical diameter of less than or equal to 1.5 mm.

A major challenge in developing such a probe is achieving the relatively high transverse resolution target, while maintaining a small diameter (e.g., 1.5 mm). For the conventional OCT catheter of FIG. 2A, the working distance and transverse resolution can be tuned by changing the object distance L1 (i.e., the distance between a distal tip of single mode optical fiber 44 and the proximal surface of GRIN lens 46). The calculated transverse resolution and working distance for such a design, as determined by Gaussian beam optics, are shown in FIG. 2B, as noted above. As indicated in FIG. 2B, the best transverse resolution for an 8-mm working distance (required for esophageal imaging), given the probe design of FIG. 2A, is about 75 µm, which is a relatively poor resolution. Systematic analysis reveals that such a relatively poor transverse resolution is primarily caused by a limited numerical aperture (NA) of the beam from the single mode optical fiber (e.g., NA~0.11), and the restriction on the GRIN lens diameter (e.g., ≦1.5 mm). In contrast, the novel concepts disclosed herein provide a catheter-sized OCT probe design that achieves a higher resolution with the same minimal form factor, by employing a miniature compound lens, in which a first lens element tightly focuses the beam and effectively increases the beam's NA (by a factor of about 2), and a second lens element that refocuses the beam with the increased NA to the desired working distance (about 8 mm for esophageal imaging, although other working distances may be desirable for different imaging applications).

FIG. 5A schematically illustrates an OCT probe 60 having a reduced form factor suitable for use in a catheter, and which employs a compound lens in order to increase a transverse resolution without increasing a relative size of the form factor, as compared to the Prior Art OCT probe of FIG. 2A. Thus, the novel OCT probe of FIG. 5A satisfies the design criteria noted above. OCT probe 60 includes housing 42, into which a distal portion of single mode optical fiber 44, a first GRIN lens 62 (having a focused beam spot size 64 at the exit surface of GRIN lens 62), a second GRIN lens 66, and a reflector 48 are disposed. An opening 50 in housing 42 enables a light beam 51 to reach a sample 68. As with conventional catheter OCT based probes, the optical elements (i.e., the single mode optical fiber, the first and second GRIN lenses, and the reflector) can be glued together using optical cement, such that L1 and L2 correspond to the thickness of the optical cement layer bonding the adjacent optical components.

Assembling multiple miniature lenses requires precision alignment, and the object distance between any two adjacent elements (e.g., L1 and L2 in FIG. 5A) should be accurately controlled. To alleviate engineering challenges and facilitate future mass production, a slightly modified OCT probe 60a (as illustrated in FIG. 5B) was designed. In OCT probe 60a, an optically transparent member 70 (preferably implemented by a glass or plastic rod) is disposed in object distance L1 (between a distal end of single mode optical fiber 44 and first GRIN lens 62). In a working model, the first GRIN lens was implemented using a miniature GRIN rod lens (or a GRIN fiber-optic lens), and the second GRIN lens was implemented using a conventional GRIN lens. Significantly, the length of the glass rod and the GRIN fiber optic lens (i.e., first GRIN lens 62) can be precisely controlled by cleaving, with an accuracy of ±5 µm (or better). The glass rod fiber (optically transparent member 70) is thermally fused to a distal end of the single mode optical fiber and a proximal end of the first GRIN lens. This configuration enables the object distance L1 to be controlled with great precision (note that as indicated in FIG. 5C and as discussed in detail below, the resolution is a function of object distance (both L1 and L2); thus, controlling the object distance with precision enables resolution to be predicted and controlled with precision). The distal end of first GRIN lens 62 is fixedly attached to a proximal end of second GRIN lens 66 using optical cement, and the distal end of the second GRIN lens is fixedly attached to the reflector using the same technique.

To tightly focus the beam from the distal end of the single mode optical fiber, a large α-value is required for the first GRIN rod (or fiber) lens, the α-value being determined using a refractive index profile relationship $n(r)=n_0(1-\alpha^2 r^2/2)$. With a GRIN fiber lens of $n_0=1.491$ and $\alpha=6.05$/mm for first GRIN lens 62, the predicted working distance and transverse resolution are graphically illustrated in FIG. 5C. These results indicate that a transverse resolution of about 30 µm can be achieved for an 8 mm working distance (required for esophageal imaging using a balloon OCT catheter) when probe 60a employs a glass rod of 0.247 mm (i.e., an object distance L1 of 0.247 mm; noting that while FIG. 5C shows L2, but not L1, a similar relationship can be graphed for L1), a 0.369 mm long GRIN fiber lens for first GRIN lens 62, a conventional GRIN lens of 0.25 pitch and a 1.0 mm diameter for second GRIN lens 66, and a separation of ~220 µm between the first GRIN lens and the second GRIN lens (i.e., object distance L2 is ~220 microns). Using these components, the diameter of all the optics will be less than 1.2 mm, achieving a form factor that can be easily integrated with a double-lumen balloon (such as those available from Wilson-Cook, Winston Salem, N.C.), having a 2.2 mm diameter transparent inner lumen, and an outer diameter of about 8 mm when the balloon is inflated.

Thus, for a probe configured as shown in FIG. 5A (or FIGS. 5B/5D/5F), four different variables determine the resolution and working distance: (1) the parameters of GRIN lens 62 (pitch and α-value); (2) the dimension of object distance L1; (3) the parameters of GRIN lens 66 (pitch and α-value); and (4) the dimension of object distance L2. These variables can be varied as desired until a useful resolution and working distance are achieved. The following exemplary techniques for defining these four variables are intended to be exemplary, rather than limiting.

The form factor of the probe will limit the diameter of GRIN lenses that can be employed (probes for relatively smaller lumens will require relatively smaller diameter GRIN lenses). Limiting GRIN lens 62 to lenses that have approximately the same diameter as the optical fiber can facilitate manufacture of the OCT probe, because thermal fusion between components having the same general diameter is relatively straightforward. As noted above, to tightly focus the beam from the distal end of the single mode optical fiber, GRIN lens 62 must also have a relatively large α-value.

In one exemplary embodiment, the first object distance L1 (optically transparent member 70 in FIG. 5B, or in some cases, a relatively thin layer of optical cement) and the pitch length of GRIN lens 62 (i.e. a GRIN fiber lens) are defined by varying the parameters of L1 and GRIN lens 62 to minimize the focused beam spot size 64 at the exit surface of GRIN lens 62, while ensuring the beam is not clipped within the glass rod (L1) or GRIN lens 62 (each of which are preferably of the same diameter of the single mode optical fiber, i.e. 125 um). Once L1 and the pitch length of GRIN lens 62 are determined, the objective distance L2 between GRIN lens 62 and GRIN lens 66, and parameters for GRIN lens 66, are then varied to achieve the designed working distance, and the transverse resolution of the entire probe can be found for the designed working distance using Gaussian beam optics.

In one exemplary, but not limiting embodiment, L2 is intentionally minimized, so that GRIN lens 62 and GRIN lens 66 are coupled together each other with optical cement (thus, L2 is implemented using optical cement).

In another embodiment, L2 is varied to include dimensions longer than can be readily implemented using optical cement, and in such embodiments an optically transparent spacer (such as a glass rod) can be used to implement L2.

If desired, a beam deflecting element 48 (if required) is attached to GRIN lens 66 with optical cement.

It should be recognized that L1 and the pitch length of GRIN lens 62 can also be selected (along with object distance L2) using Gaussian beam optics with a multiple parameter search, so that the smallest focused beam spot is achieved at the final desired working distance (e.g. 8-15 mm) without causing beam clipping within the glass rod and the GRIN fiber lenses.

A unique feature of such a balloon imaging catheter (i.e., as shown in FIG. 4) is its large working distance, which is achieved while still maintaining a small focused spot size (i.e., high lateral resolution) and a small diameter (permitting the deployment of the balloon catheter into the esophagus through the standard accessory port of a GI endoscope). Such an OCT imaging catheter enables high-resolution circumferential imaging of the entire human esophagus. Compared to a single lens catheter design (FIG. 2A) where either a long or short pitch GRIN lens is used, the disclosed compound lens catheter design (1) offers a much better transverse resolution at a given long working distance (e.g. by about a factor of 2); and (2) facilitates designing probes suitable for mass production. As noted above, the large working distance, high lateral resolution, and small overall diameter are achieved by using a compound lens made of several rod lenses and spacers (FIG. 5B; noting that a spacer can be disposed between GRIN lens 62 and GRIN lens 66 when L2 is larger than can be accommodated using optical cement). Note that implementing L1 or L2 using optical cement is very challenging, if the object distance (i.e., L1 or L2) is larger than the diameter of the smaller of the GRIN lens (or optical elements) being joined. Furthermore, optical cement is not as mechanically robust or stable as thermal fusion, thus when possible thermal fusion is preferred.

A significant feature of the OCT probe designs disclosed herein is that thermal fusion can be used to connect at least some elements. In an exemplary fabrication technique, a glass rod spacer used to implement L1 is thermally fused to a single-mode fiber, and then cleaved to the desired dimension for L1. The glass rod is then fused to the GRIN fiber (or rod) lens used to implement GRIN lens 62. That GRIN lens (i.e., GRIN lens 62) is then cleaved at the desired pitch length. GRIN lens 66 is coupled to GRIN lens 62 with optical cement, with the object distance L2 precisely tuned (e.g. by a precision micron translation stage) to achieved the designed working distance. Where L2 is implemented with a spacer, that spacer and GRIN lens 66 can be similarly fused together and precisely cleaved, followed by joining [spacer (L1)+GRIN lens 62] to [spacer (L2)+GRIN lens 66)] together with optical cement, enabling precise control of the dimension of L1 and L2, and the pitches (i.e., lengths) of each GRIN lens. When coupled in series, these components create a compound lens that enables the catheter to achieve the desired working distance, while maintaining an acceptably small focused spot size. A micro-prism or beam deflector is used to redirect the beam 90°, into the tissue. A prototype of such an OCT probe was successfully constructed and exhibited a working distance of 9.6 mm, and a measured focused spot size of 39 µm.

Circumferential OCT imaging can be performed by rotating the imaging catheter of FIG. 4 within the double lumen balloon. To systematically image a segment of an esophagus of interest, a spiral scanning pattern can be achieved by pulling back the OCT catheter while it is being rotated. This approach is analogous to spiral CT and 3-D intravascular ultrasound (IVUS) imaging. The 3-D structure of the esophageal wall can be reconstructed from the spiral scan by using standard computer interpolation algorithms. A computer-controlled direct current (DC) motor with an accurate position encoder can be used to perform pull-back. The pull-back speed will depend on the imaging acquisition speed, the circumferential pixel density, and the spiral scan pitch. Assuming an OCT axial scanning speed of 30,000 A-lines per second (achievable with a swept source or spectral domain OCT) and a circumferential pixel size of 20 µm (e.g., about half of the transverse resolution), each circumferential scan will take about $2\pi*8$ mm/20 µm(30,000 $s^{-1}$), or about 0.08 seconds for a balloon having an 8 mm radius. If the spiral scan pitch is 50 µm, a pull-back speed of about 0.6 mm/sec would be required, which is readily achievable. The rotation, pull back and data acquisition can be controlled and synchronized by software for the spiral 3D imaging.

A key component for implementing circumferential scanning is a fiber-optic rotary joint, which couples light from a rotating catheter to a stationary source fiber. The rotary joint is disposed at a proximal end of a catheter, providing a convenient way to switch catheters. A working exemplary prototype embodiment of a compact rotary joint having dimensions of about 1.5 cm in diameter and about 8 cm in length has been successfully fabricated. Such a rotary joint can be coupled to a spiral-scan pull-back motor and incorporated into a single handheld unit, facilitating manipulation of the balloon imaging catheter of FIG. 4. This type of handheld unit will be suitable for use in an in vivo or a clinical environment. Alternatively, mechanisms for rotating the micro-prism or reflector disposed at the distal end of the OCT probe could be employed to achieve the circumferential scanning, with a lateral translation stage being employed to achieve the spiral scanning.

As noted above, precise control of L1 and L2 enables specific resolutions and working distances to be achieved. FIG. 5D schematically illustrates an OCT probe 60b in which variations in L2 enable different working distances and resolutions to be achieved, as graphically indicated in FIG. 5C. OCT probe 60a includes single mode optical fiber 44, first GRIN lens 62, a spacer 45 disposed between the optical fiber and the first GRIN lens (i.e., spacer 45 is L1), second GRIN lens 66, a spacer 47 between the first GRIN lens and the second GRIN lens (i.e., spacer 47 is L2), and reflector 48. Spacer 47 can be implemented by a controlled thickness of an adhesive such as optical cement, a physical spacer having a predefined thickness (such as a cylindrical or ring shaped plastic mass), or a combination of cement and physical spacer. Exemplary techniques for determining the lengths (L1, the length of the GRIN fiber lens and L2) are described above.

FIG. 5F schematically illustrates an OCT probe 60c in which GRIN lens 66 has a relatively shorter pitch length, and the desired dimension of a spacer for L2 is sufficiently large that the use of optical cement alone would be impractical. The relationship between L2, working distance and resolution for OCT probe 60c is graphically indicated in FIG. 5E. OCT probe 60c includes single mode optical fiber 44, first GRIN lens 62, spacer 45 disposed between the optical fiber and the first GRIN lens (i.e., spacer 45 is L1), second GRIN lens 66, a spacer 49 between the first GRIN lens and the second GRIN lens (i.e., spacer 49 is L2), and reflector 48. Spacer 49 is implemented using a plastic or glass rod that is substantially transparent to the wavelengths of light that are emitted and received by OCT probe 60c, because spacer 49 is too long to implement using optical cement alone.

FIG. 6 schematically illustrates an OCT system incorporating the OCT probe of FIG. 5B, to enable esophageal OCT imaging to be used to systematically detect Barrett's and sub-squamous Barrett's esophagus, using either circumferential scanning or spiral three-dimensional scanning, generally as discussed above. A system 110 includes an OCT probe 112 (substantially similar to the esophageal OCT catheter probes discussed above), a rotary joint 114, a pull-back stage 116 (with one or more prime movers to rotate and linearly translate the OCT probe, the rotary joint and pull-back stage optionally being enclosed in a common housing 115), a controller 118 (e.g., implemented using a processor and a memory storing machine instructions executed by the processor, although such a controller can also be implemented using a custom logic circuit), and additional required OCT components (generally consistent with the OCT system of FIG. 1). The prime mover can rotate the rotary joint via a timing belt, and the rotary joint along with the prime mover can be linearly translated using a precision motorized stage. The combination of rotation and linear translation achieves a spiral beam scanning pattern for performing spiral 3-D volumetric imaging.

Real-time OCT imaging using a balloon catheter based on the exemplary embodiments of FIGS. 4 and 5B was experimentally demonstrated using a standard swept source OCT system modified to generally correspond to the system of FIG. 6. This exemplary OCT system utilized a 1310 nm swept laser source with a Full Width at Half Maximum (FWHM) bandwidth of 106 nm and a sweeping frequency of 6 kHz, corresponding to an imaging speed of 12,000 axial scans per second. The line width of the swept source is about 0.15 nm corresponding to an imaging depth of ~2 mm. The measured axial resolution was 8.5 µm. The system had a signal-to-noise ratio of about 120 dB at 6.5 mW incident power on the sample. In a test of this system, OCT images from a pig esophagus were acquired. The deflated balloon catheter was inserted into the pig esophagus and then fully inflated.

FIG. 7A is a circumferential esophageal OCT image of a pig esophagus acquired using the system described above (i.e., a system substantially identical to that illustrated in FIG. 6), illustrating that circumferential esophageal OCT imaging is achievable. The image size is ~2 mm×60 mm (2000×3000 pixels, axial x circumferential). Note that the void space in the middle of the image is not to actual scale, the void has been included purely for the purpose of enlarging the display of the tissue portion of the image. The imaging frame rate was 4 Hz, which can be significantly improved upon by using a faster swept source or spectral domain OCT system. The identifiable layers include the epithelium (E) 124, lamia propria (LP) 126, muscularis mucosa (MM) 128, submucosa (SM) 130, and muscularis propria (MP) 132.

FIG. 7B is an esophageal OCT image of a pig esophagus acquired using the system described above (i.e., a system substantially identical to that illustrated in FIG. 6), illustrating that three-dimensional spiral esophageal OCT imaging is achievable (note that the pitch displayed is not to scale, since the Figure is purely for illustration). The experimental pitch length of the spiral is about 20 µm.

The exemplary balloon imaging catheter (based on FIGS. 4 and 5B) provides 2-D and 3-D images of esophageal tissue. The catheter overcomes limitations in conventional OCT endoscope design and provides a simple scan mechanism, permitting methodical imaging of the entire esophagus for Barrett's (surface and sub-squamous) surveillance and cancer detection to be achieved. Using such apparatus, OCT imaging can be used to detect Barrett's esophagus, and for analyzing the collected images for structures corresponding to the sub-squamous Barrett's glands of FIG. 3C. As discussed in detail above, in ex vivo images such sub-squamous Barrett's structures could be mistaken for blood vessels, but during in vivo imaging, the presence of blood flow will enable blood vessels and Barrett's structures to be easily differentiated.

Other configurations of a compound fiber-optic lens for achieving a relatively high resolution at a desired working distance are also possible. Furthermore, the same general principles can also be used to focus the OCT beam at relatively shorter working distances, such as those required in an intravascular catheter for imaging a small vessel or for interstitial imaging with a much higher spatial resolution. Such an exemplary embodiment is schematically illustrated in FIG. 8. The compact form factor, shorter working distance, and high spatial resolution are achieved by using a compound lens comprising three different GRIN lenses. While additional GRIN lenses could be employed, it should be noted that optical losses are associated with the connecting (e.g. by thermal fusion) multiple GRIN lenses, and employing more than three GRIN lenses to achieve a compound lens may lead to unacceptable optical losses.

Referring to an OCT probe 72 of FIG. 8, a distal end of a single mode optical fiber 78 is stripped of its protective coating 76, and is coupled to a compound lens formed of three GRIN lenses 80, 82, and 84. A reflector 86 directs a light beam 88 through an opening in a housing 74 toward a sample 90. Preferably an optical window 73 fills the opening, although an inner optically transmissive housing encompassing the compound lens can also be employed. Fabrication of OCT probe 72 is accomplished by thermally fusing a distal end of single mode optical fiber 78 to GRIN lens 80, and thermally fusing GRIN lens 80 to GRIN lens 82. GRIN lens 84 is coupled with GRIN lens 82 either by thermal fusion (or by using optical cement if the thermal fusion loss is not acceptable due to the mismatch of the diameters). The design concept is generally the same as discussed above with respect to the exemplary OCT probes of FIGS. 5A and 5B, in that the proximal compound lens elements (GRIN lenses 80 and 82) tightly focus light emitted from the distal end of the single mode optical fiber, while the distal lens element (GRIN lens 84) refocuses the beam to a desired working distance with a high transverse resolution.

The details of exemplary OCT probe 72 are as follows. GRIN lens 80 is implemented using a 0.25-pitch length lens that collimates the beam from the single mode optical fiber. GRIN lens 82 is also implemented using a 0.25-pitch length lens; however, the middle GRIN lens has more focusing power (e.g., GRIN 82 has a larger α-value than does GRIN lens 80). GRIN lens 82 focuses the collimated beam to a smaller spot at its exit surface, and the new focused spot size is provided by the following relationship:

$$D_2 = \frac{n_{o1}\alpha_1}{n_{o2}\alpha_2} D_1 \qquad (1)$$

where $D_1$ is the input spot size for GRIN lens 80 (i.e., the mode field diameter of the single mode optical fiber), $\alpha_1$ is the α-value of GRIN lens 80), $\alpha_2$ is the α-value of GRIN lens 82, $n_{o1}$ is the on axis refractive index of GRIN lens 80, and $n_{o2}$ is the on axis refractive index of GRIN lens 82.

GRIN lens 84 has a lower focusing power than the other GRIN lenses, but a larger aperture, and GRIN lens 84 images the focused spot D to a final focused spot. Significantly, the pitch number of GRIN lens 84 can be selected to achieve a desired working distance. Customized GRIN fiber lenses (having a diameter of about 125 microns) can be used to implement GRIN lenses 80 and 82, and a commercially available GRIN lens (having a diameter of about 250 μm) will be used to implement GRIN lens 84. The single mode optical fiber, GRIN lens 80, and GRIN lens 82 will be thermally fused in tandem, and each of GRIN lens 80 and GRIN lens 82 will be precisely cleaved to achieve a 0.25 pitch length. Because the aperture of GRIN lens 84 is larger than the aperture of the other GRIN lenses, beam vignetting within GRIN lens 84 is prevented. GRIN lens 84 is attached directly to GRIN lens 82 with optical cement, and no appreciable space is required between the two. Based on the above parameters, Gaussian calculations indicate that the final beam focused spot size will be about 7.1 microns, at a working distance of about 500 microns, using a 0.327-pitch length GRIN lens for GRIN lens 84. Significantly, such a spot size represents a 200% reduction (i.e., improvement) compared to a traditional single GRIN lens approach. The resultant high transverse resolution will be appreciated when considering the small optics diameter (125-250 microns) and the working distance achieved (e.g. 500 microns, which is sufficient to enable the focus to be disposed in tissue that can be placed in direct contact with the beam window of the miniature probe). This transverse resolution will be close to the axial resolution produced by the 1300 nm light source commonly employed in OCT systems. All three GRIN lenses and the reflector can be encased within a protective glass tube (a durable quartz glass having good optical and structural properties is employed in an exemplary embodiment). Previous designs have employed polished optical cement for the optical window. However, polished optical cement can be easily scratched, significantly reducing optical clarity and the service lifetime of the imaging probe. The use of a glass housing eliminates this problem. If desired, matching fluid can be used to fill any void spaces within the glass housing to reduce undesired back reflection or beam profile distortion.

Yet another aspect of the present invention is directed to incorporating OCT imaging into needle biopsy probes, to achieve image guided needle biopsy. Such technology can perform high-resolution, microscopic imaging of biological tissues in vivo and in real-time. This technology will permit real-time assessment of the tissue in situ by providing structural and/or quantitative information before tissue removal, leading to improved tissue sampling accuracy and reduced biopsied tissue volumes, thereby making biopsy less invasive.

It should be noted that in addition to high-resolution imaging of tissue microanatomy in situ, it has been demonstrated that the depth-dependent OCT signals can be analyzed to obtain localized tissue optical properties, which are related to cellular morphologies such as the shape, size and density of the cell organelles and nuclei. Significantly, such properties can be altered by neoplastic changes, and thus such properties might be used to detect morphological changes. The quantitative information can then provide objective evaluation of the target "suspicious" tissue. This can be very complementary to structural imaging, in particular, when the lesion is homogeneous as in the case of poorly differentiated adenocarcinoma. The quantitative information would also allow systematic comparison between normal and pathologic tissues. The high-resolution morphologic imaging and the quantitative information about localized tissue optical properties enhance the OCT needle probes capability of targeting pathologic tissues of small volumes for biopsy.

As disclosed herein, the development of a 27-gauge (or 400 μm diameter) OCT imaging needle enables interstitial high-resolution imaging of solid tissues/organs beyond a depth of 1-3 mm, which is about as deep as can be achieved when performing OCT imaging from outside the tissue. The OCT imaging needle includes passive fiber-optic components, and can be directly introduced into tissue with no electric hazard. Preliminary studies have demonstrated that the small diameter of the OCT needle does not cause visible bleeding or trauma when introduced into solid tissue.

FIG. 9 schematically illustrates an exemplary OCT image-guided biopsy probe 150 that includes an imaging needle 152, with OCT optics, and a biopsy needle 154 (including a biopsy window 156, configured to extract a relatively small portion of tissue for analysis). OCT image-guided biopsy probe 150 can be positioned proximate a mass of tissue 158, so that needle 152 can be advanced into the tissue. An optical beam 160 emitted from a distal end of needle 152 enables a generally cylindrical region of tissue 162 to be imaged (by rotating the optics in the needle, generally as discussed above with respect to circumferential and 3-D spiral scanning). Should any of the imaged tissue indicate a sample of tissue is required, biopsy needle 154 is advanced into the tissue to obtain a sample.

Significantly, when imaging needle 152 is implemented using a 27-gauge needle, the resulting imaging needle is significantly smaller than conventional 11-18 gauge core biopsy needles. The small size and the capability of imaging tissue micro-anatomy make such an OCT imaging needle an excellent candidate to be integrated with a biopsy needle, for providing image guidance in situ. Interstitial imaging can be performed by rotating the needle using a computer controlled precision DC motor with the image plane perpendicular to the rotation axis, generally as discussed above with respect to esophageal scanning. Imaging at various planes can be achieved by inserting or retracting the OCT needle and a 3-D image can be constructed using well-established computer algorithms such as are used in spiral CT. An imaging penetration depth of approximately 1-3 mm results in a cylindrical imaged tissue volume of 2-6 mm in diameter and several millimeters to centimeters in length with a single needle insertion. This result is a significant improvement compared to what is provided by taking a 1-mm diameter core biopsy specimen in a conventional approach. Since the imaged area scales as the square of the diameter, needle-based OCT can evaluate volumes 4 times to 36 times larger than that of a single 1 mm diameter core biopsy. As noted above, the OCT imaging needle is inserted through the biopsy needle into the lesion, and high-resolution interstitial images are then taken along the insertion path. Upon identification of a suspicious region (by structural imaging and/or quantitative tissue optical properties), the core biopsy needle can then slide over the OCT needle to the target region to withdraw a biopsy sample. The OCT imaging needle will then be retracted and standard tissue biopsy can then be performed on the specimen taken. The relatively small size of such an OCT needle would dramatically reduce the chance of blocking the conventional image-guidance for directing needle biopsy.

FIG. 10A schematically illustrates an OCT probe 164, where an outer housing 166 comprises a 27-gauge hollow steel needle having a sharpened tip 168. A distal end of a single mode optical fiber 170 is coupled to a 250 micron diameter GRIN lens 172 using a layer of optical cement 179. Lens 172 directs a light beam 176 from the single mode optical fiber to a reflector 174, through an optical window 177 made of polished optical cement (which also attaches lens 172 to reflector 174) toward a sample 178. FIG. 10B shows the size of OCT probe 164 relative to a U.S. ten cent coin 180 (i.e., a dime).

Key design parameters considered in developing exemplary OCT probe 164 included: (1) the imaging beam focused spot size (which determines the transverse resolution); and, (2) the working distance, which is the distance between the distal end-surface of the GRIN lens to the beam focus. For a given GRIN lens, the focused spot size and working distance are controlled by the "object distance," i.e., the separation between the single mode optical fiber tip and the GRIN lens. FIG. 10D graphically illustrates these two parameters versus the object distance, as calculated using Gaussian optics. A standard parabolic refractive index of the GRIN lens was used for the calculation, e.g., $n(r)=n_0(1-\alpha^2 r^2/2)$ where r is the distance from the lens center, $n_0=1.4685$, $\alpha=1.6$/mm, and the length of the GRIN lens is quarter-pitch (i.e., $0.25*2\pi/\alpha=0.9817$ mm). Notice that an increase in the object distance will result in a smaller focused spot size (or a higher transverse resolution), and a shorter working distance. In general, once the required working distance is determined, the relationships illustrated in FIG. 10D can be used to determine the object distance that will enable the required working distance to be achieved, while also enabling a determination to be made as to whether the selected working distance/object distance combination will achieve an acceptable resolution (spot size), for a given GRIN lens. The required shortest working distance will be equal to the needle diameter, in order to have the beam focus outside of the needle. Considering a 27-gauge needle (~400 μm in diameter), an optimal working distance of ~500 μm was selected, to enable the OCT needle imaging probe to have the flexibility to set the position of the focal point outside the optical window (e.g., by adjusting the distance between the GRIN lens and the 90° reflector). According to FIG. 10D the smallest focused spot size corresponding to a 500 μm working distance will be 11 μm.

FIG. 10C shows an OCT image obtained using an exemplary prototype device corresponding to OCT probe 164. Significantly, fine structures such as muscle fibers 182 can be seen in the image. Imaging was performed using a 1300 nm light source with axial resolution of ~5 μm (in tissue). The sector image includes 625×1250 pixels (i.e., circumferential× radial). No bleeding from needle insertion was observed as the image was acquired. It should be noted that the image was obtained using an optical window comprising polished optical cement (i.e., a relatively poor quality optical window). Improvements in distal end beam focusing optics and optical window design should yield significant improvements in image quality. OCT probe 164 is small (~400 μm in diameter) and can easily pass through the core of an 18-gauge biopsy needle, which has an inner diameter of about 1.6 mm.

Some limitations were identified in the prototype exemplary OCT imaging needle design (i.e., the prototype based on OCT probe 164). It was of limited durability, and it was difficult to control the imaging beam parameters and quality. In the prototype, the optical components at the needle's distal end were glued together, and an optical window was produced by polishing the optical cement disposed at the distal end. Because optical cement is not as strong as glass, the optical window surface was easily damaged/scratched when the needle was introduced into soft tissue, causing severe degradation of image quality or failure to acquire any image at all. In addition, the miniature GRIN lens (250 μm in diameter) was assembled manually (i.e., joined to the distal end of the single mode optical fiber and coupled to the reflector) within the needle, making it extremely difficult to control the position of the GRIN lens relative to the other miniature optical components. Consequently, imaging beam parameters, such as the focused spot size and the working distance, were difficult to adjust, and these parameters were often achieved by trial and error. The engineering protocol was delicate and tedious, resulting in high fabrication costs, rendering the design impractical for mass production.

One technique to improve the mechanical stability of the needle OCT probe, and to simplify fabrication, is to thermally fuse the GRIN lens with the single mode optical fiber. This approach will eliminate the object distance between those elements, and the imaging beam parameters can then be controlled purely by the pitch number of the GRIN lens (for a given refractive index profile). A further improvement is to encapsulate the optical components in a glass inner housing (which provides structural support as well as a high quality optical window), which can then be inserted into an outer hollow (metal) needle. FIG. 11 schematically illustrates such an exemplary OCT probe 190, where an inner housing 192 comprises a quartz glass tube having a diameter sufficiently small to enable the quartz glass tube to fit inside the 27-gauge hollow steel needle employed in OCT probe 164 of FIG. 10A. A distal end of single mode optical fiber 170 is thermally fused (thus eliminating any object distance at this location) to a 125 micron diameter GRIN lens 172a. Note that use of the smaller GRIN lens relative to probe 164 of FIG. 10A (125 μm diameter vs. 250 μm diameter) enables the optics to be placed inside the quartz glass tube inner housing. GRIN lens 172a directs light beam 176 from the single mode optical fiber to reflector 174, through the quartz glass tube (which functions as a housing and a high quality optical window) and a beam window 173 (i.e., an opening in the hollow steel needle; noting that if the inner transparent tube is not employed, beam window 173 can be filled with an optically transmissive material, rather than simply being an opening) toward a sample 178. Preferably, the GRIN fiber lens, which has the same bare optical fiber diameter as the single mode optical fiber (e.g., 125 μm in diameter), which in addition to fitting inside the quartz glass tube also facilitates alignment during thermal fusion. After fusing the single mode optical fiber and the GRIN fiber lens, the GRIN lens can be cleaved at the appropriate length, according to the designed focused spot size and working distance.

In theory, the index of refraction of the GRIN lens approximately follows a parabolic profile (i.e., $n(r)=n_0(1-\alpha^2 r^2/2)$). Probe 190 can utilize a customized GRIN fiber lens, which has a smooth refractive index profile as described by the above equation. Using Gaussian optics, the working distance and the focused spot size versus the pitch number of the GRIN fiber lens can be calculated. Again, an optimal working distance of ~500 μm is selected (for a 27-gauge needle), and this configuration leads to a corresponding focused spot size (or transverse resolution) of approximately 14.5 μm, when a 0.36-pitch (or 1.41 mm long) GRIN fiber lens is used. The fusion junction between the single mode optical fiber and the GRIN lens has proven to be mechanically strong and optically transparent. Such fabrication techniques are straightforward, fast, cost-effective, and no manual alignment is required.

Significantly, the use of a quartz glass inner housing (inner in that the quartz glass housing, while encompassing the OCT optics, is designed to fit within the outer 27-gauge hollow needle) solves the durability issue for the optical window. Once the single mode optical fiber is fused with the GRIN fiber lens, those elements and the micro reflector are introduced into a small fused silica tube (e.g., of an inner diameter of 150-250 µm and a wall thickness of 100-50 µm). The inner glass housing is then placed into (and secured using glue, epoxy, or optical cement) the hypodermic needle, which includes a pre-cut opening through which light can pass. For interstitial imaging, the fused silica tube will be in direct contact with the tissue, and the glass is much more scratch-resistant than the polished optical cement window of OCT probe 164. Stainless hypodermic tubes of different sizes (23-gauge to 27-gauge) or wall-thickness can be chosen to achieve desired mechanical strength and flexibility. The distal end of the hypodermic tube will be sharpened to facilitate the needle insertion into solid tissues.

As indicated in FIG. 10D, the focused spot size can be reduced by increasing the distance between a given GRIN lens and the distal tip of the single mode optical fiber. In order to stabilize the space between the distal tip of the single mode optical fiber and a GRIN lens required to achieve a desired object distance, in some exemplary embodiments (as exemplified by FIG. 13, which is described in greater detail below) a glass rod (for example, one having an outer diameter substantially equal to that of the single mode optical fiber) will be thermally fused to the distal end of the single mode optical fiber and a proximal end of the GRIN fiber lens. Note that the input beam spot size at the entrance surface of the GRIN lens fused to the spacer will be larger after passing through the spacer; thus, the numerical aperture of that GRIN lens can be fully utilized to achieve a tighter focus. If care is taken when choosing the length of the spacer, the beam diameter within the GRIN lens will remain smaller than a core diameter of the GRIN lens. Assuming the core diameter of the GRIN lens is 110 µm, calculations based on Gaussian optics reveal that the longest permissible glass spacer is 0.64 mm (to fully utilize the numerical aperture of the GRIN lens). Once the spacer length is fixed, the working distance and the focused spot size can be controlled by the pitch number of the GRIN lens. The relationships between working distance and spot size versus the pitch number are graphically illustrated in FIG. 12. Note that for a 500 µm working distance, a focused spot size of 9.9 µm can be achieved with a GRIN lens of a length 0.234 pitch (or 0.92 mm), which represents an ~32% spot size reduction compared to the previous approach without using a glass spacer (as shown in FIG. 10A which had a transverse resolution of about 14.5 µm). The fabrication procedure will again be straightforward and will include the following steps: (1) thermally fuse the glass spacer with the distal end of the single mode optical fiber; (2) cleave the glass spacer at a precise length (e.g., 0.64 mm in this example); (3) thermally fuse the GRIN fiber lens to the glass spacer; (4) cleave the GRIN fiber at a precise length (e.g., 0.92 mm); and, (5) encapsulate the distal end of the single mode optical fiber, the spacer, the GRIN lens, and a micro-reflector in a quartz glass capillary tube. Although the lengths of the glass spacer and the GRIN lens are relatively short, empirical studies indicate that a cleaving accuracy of +/−5 µm can readily be achieved with a motorized fiber cleaver.

FIG. 13 schematically illustrates an exemplary OCT probe 194 (for incorporation into a needle biopsy probe), in which a distal end of single mode optical fiber 170 is thermally fused to a spacer 196, which in turn, is thermally fused to a 125 micron diameter GRIN lens 198 (GRIN lens 198 differing from GRIN lens 172a of FIG. 11 by having a different pitch and/or a refractive index profile), which directs the light beam from the single mode optical fiber to reflector 174, through quartz glass housing 192 (which functions as a housing and a high quality optical window), and toward a sample 178 through beam window 173 (i.e., an opening in the needle; noting that if the inner transparent tube is not employed, beam window 173 can be filled with an optically transmissive material, rather than simply being an opening).

The focused spot size can be further reduced, even with maintaining the required minimum working distance, if a compound GRIN lens is employed. In this approach, a micro compound lens includes a plurality of GRIN (fiber) lenses of different refractive index profiles and clear apertures. In general, two or three different GRIN lenses work best, since if more than three GRIN lenses are employed, the optical losses become unacceptably high. FIG. 14 schematically illustrates an OCT probe 200 (for incorporation into a needle biopsy probe), in which a distal end of single mode optical fiber 170 (with its protective cladding 169 removed) is thermally fused to a first GRIN lens 202. First GRIN lens 202 is then thermally fused to a second GRIN lens 204. A 250 micron diameter GRIN lens 206 is coupled to a distal end of second GRIN lens 204, to direct a light beam from the single mode optical fiber to a reflector 174, through a quartz glass housing 192a toward a sample 178. Quartz glass housing 192a functions as a housing and a high quality optical window and is slightly larger in size than the glass housings discussed above, to accommodate the larger 250 micron diameter GRIN lens. Of course, if desired, beam window 173 (i.e., an opening in the needle) could be filled with an optically transmissive material, rather than simply being an opening, particularly if the inner transparent tube is not employed). An exemplary production sequence is as follows: thermal fusion of single mode fiber 170 with GRIN lens 202; cleaving of GRIN lens 202 to a desired length; thermal fusion of GRIN lens 202 with GRIN lens 204; cleaving of GRIN lens 204 at a desired length; connecting GRIN lens 204 with GRIN lens 206 using a predetermined length of optical cement (or via thermal fusion if the loss is acceptable).

First GRIN lens 202 can have a 0.25-pitch length and will collimate the beam from the single mode optical fiber. Second GRIN lens 204 also can have a 0.25-pitch length and is implemented using a lens with more focusing power (e.g., with a larger α-value) than first GRIN lens 202. Second GRIN lens 204 focuses the collimated beam to a smaller spot at its exit surface, and the new focused spot size is found using Eq. (1), where $D_1$ is the input spot size for the first GRIN lens (i.e., the mode-field diameter of the single mode optical fiber); $\alpha_1$ is the α-value for first GRIN lens 202, $n_{01}$ is the on-axis refractive index of first GRIN lens 202, $\alpha_2$ is the α-value for second GRIN lens 204, and $n_{02}$ is the on-axis refractive index of second GRIN lens 204. The larger and most distal GRIN lens 206 has a lower focusing power, but a larger aperture, and images the focused spot $D_2$ to a final focused spot. The pitch number of GRIN lens 206 can be selected to achieve a desired working distance. The first and second GRIN lenses are preferably implemented using customized GRIN fiber lenses (with a 125-µm diameter), and a commercially available rod lens is used to implement GRIN lens 206 (250 µm in diameter).

The single mode optical fiber, first GRIN lens 202, and second GRIN lens 204 are thermally fused together. The pitch lengths of the first and second GRIN lenses are then precisely cleaved to be 0.25. Note that because the aperture of GRIN lens 206 is larger (250 μm vs. 125 μm), beam vignetting (or clipping) within GRIN lens 206 is prevented. Preferably, GRIN lens 206 is attached directly to GRIN lens 204 with optical cement, and no space (object distance) is required between the two. Thermal fusion of the two GRIN lenses together is also possible if the optical loss is acceptable. Calculations indicate that when the above optical parameters are employed in conjunction with GRIN lens 206, which has a 0.327-pitch length, the final beam focused spot size should be 7.1 μm, at a working distance of 500 μm. Such a spot size represents ~30% reduction compared to the approach using a glass spacer and a single GRIN lens (i.e., as shown in FIG. 13). The resultant relatively high transverse resolution will be appreciated when considering the relatively small optics diameter (125-250 μm), and the working distance of 500 μm, which is quite sufficient for an extremely small imaging needle/probe. Such a transverse resolution is relatively close to the axial resolution produced by the 1300 nm light source commonly used in OCT imaging systems. The three GRIN lenses and the reflector can be encased within a quartz glass tube (or other optical clear and durable glass or plastic enclosure), so that an optical window of glass (or plastic) is provided for enhanced durability. Note that a transparent index matching fluid can be added to within the hypodermic tube to reduce beam back reflection and distortion at the probe optical window.

A summary of the focused spot size for the three designs discussed above (i.e., FIGS. 11, 13 and 14) is given in Table 1, where the working distance is all fixed at 500 μm.

TABLE 1

Focused Spot Size for Three Needle Design Configurations

| Configuration | FIG. 11<br>SFM + GRIN | FIG. 13<br>SMF + Spacer +<br>GRIN | FIG. 14<br>SMF + GRIN1 +<br>GRIN2 + GRIN3 |
|---|---|---|---|
| Glass Spacer | 0 | 0.64 mm | 0 |
| Length of<br>GRIN Lens<br>and α-value | 0.36-pitch<br>α = 1.6/mm | 0.234-pitch<br>α = 1.6/mm | GRIN1: 0.25-pitch,<br>α = 2.2/mm<br>GRIN2: 0.25-pitch,<br>α = 6.05/mm<br>GRIN3: 0.327-pitch,<br>α = 2.31/mm |
| Spot Size (μm) | 14.5 | 9.9 | 7.1 |

With respect to the OCT guide needle biopsy embodiments, a circumferential image of tissue internal microstructure is acquired by rotating the OCT imaging needle. The needle can be rotated continuously in one direction (e.g., either clockwise or counter-clockwise) using a DC motor. A rotational coupler/rotary joint can be used to couple light from a stationary optical fiber to a rotating needle. Three-dimensional data sets can be obtained by pulling back the imaging needle while it is being rotated, in a spiral pattern analogous to a spiral CT or a pullback-mode intravascular ultrasound (IVUS), generally as discussed above with respect to esophageal OCT imaging.

In such embodiments, potential imaging limitations include spherical and chromatic aberrations, and a cylindrical lens effect caused by the glass housing/tube. It has been shown that the GRIN lenses employed in the above needle biopsy embodiments exhibit negligible spherical aberration, in particular when the beam goes through the GRIN lens symmetrically with respect to the lens longitudinal axis. However, GRIN lenses do exhibit chromatic aberration, resulting in a loss of OCT axial (and transverse) resolution. Compared to shorter wavelengths (e.g., visible or near 800 nm), GRIN lenses are less dispersive at 1300 nm, and thus exhibit less chromatic aberration at 1300 nm. Resolution degradation due to chromatic aberration can be characterized with a broadband light source by measuring the change of the spectrum back-reflected at different positions across the focal plane. In principle, special glasses (e.g., Gradium™ glass from LightPath Technology) can be used to minimize the chromatic aberration, and micro GRIN lenses can be fabricated from such materials.

The glass tube in which the micro optical components (such as the single mode optical fiber, the GRIN lens(es), the glass rod spacer and the micro reflector) are housed, will introduce a diverging cylindrical lens effect along a direction perpendicular to the tube's longitudinal axis. This effect is expected to be reduced when the window is in direct contact with tissue (due to rough index "matching"). Furthermore, the lens effect caused by the inner surface of the glass tube can be reduced by using an index-matching fluid to fill the space between the GRIN lens and the micro reflector within the glass tube, and calculations confirm that such an index-matching fluid will not substantially affect the focused spot size and working distance.

In addition, the outer surface of the tube can be slightly polished to achieve a flat optical window where the light beam exits the glass tube. Such embodiments will likely require a thicker walled glass tube (e.g., ~100 μm), which will increase the needle diameter by about 100-150 μm; but the overall size will still be sufficiently small enough to fit inside a 23-gauge hollow needle, thereby still permitting integration of the imaging needle with a core biopsy needle of 14-18 gauge.

FIG. 15A schematically illustrates an exemplary OCT system 210 incorporating the biopsy needle and OCT imaging probe of FIG. 9 (where the OCT imaging probe can be implemented using any of the exemplary embodiments of FIGS. 10A, 11, 13, or 14), to enable OCT imaging to guide needle biopsies, using circumferential scanning or spiral 3-D scanning, generally as discussed above. Note OCT system 210 is similar to OCT system 110 of FIG. 6, differing primarily in regard to the OCT optics used and OCT probe form factor. OCT system 210 includes an OCT probe and biopsy needle 212 (substantially similar to the combination of FIG. 9), an optional rotary joint 114, a pull-back stage 116 (with one or more prime movers to rotate and linearly translate the OCT probe), controller 118 (which can be implemented using a processor and a memory storing machine instructions, or a custom circuit), and additional appropriate OCT components 120 (generally consistent with the OCT system of FIG. 1). The rotary joint is considered optional, because in some exemplary embodiments, where the needle outer housing of the OCT needle probe is sufficiently long, the housing itself might be rotated by a prime mover, instead of requiring the single mode optical fiber to be rotated (which will likely require a rotary joint).

FIG. 15B schematically illustrates one possible exemplary implementation of OCT system 210 (the processor and additional OCT components not being shown). OCT imaging needle 222 passes through biopsy needle 224 and is actuated (or rotated) with a DC motor 232 (which drives a shaft 234 and gears 230). If desired, a proximal end of OCT imaging needle 222 and the DC motor can be encompassed in a housing 228. OCT imaging needle 222 (along with the DC motor) can be translated by a linear motor 220 that is coupled to a translation stage or plate 236 (for controlling the insertion depth). The platform also guides the insertion of both needles in a common, single direction. A support 226 facilitates directional control and support of the imaging needle and the biopsy needle. Support 226 can include a central guiding barrel. The biopsy needle will first be placed within the guiding barrel on the platform and locked in place with a setscrew (not separately shown). Ruler ticks can be incorporated on the outer surface of the biopsy needle, starting at its proximal end, for measuring the insertion depth. The OCT imaging needle will then pass through the biopsy needle and be advanced into the sample. Note that the distal end of the core biopsy needle will have a small channel for the OCT needle to pass through. The platform that integrates both needles will be fixed on a stereo tactic frame for controlling the needle's lateral position and orientation.

The exemplary steps of the operational procedure for the OCT image-guided biopsy are as follows: (1) adjust the OCT imaging needle position and orientation so that the imaging beam exits the center of the biopsy needle opening, and record the positions of both needles; (2) advance the OCT imaging needle into the sample, and once the region of interest is identified, stop advancing the OCT needle and record the current depth and imaging beam direction; (3) align the biopsy needle opening with the current imaging beam direction, and slide the biopsy needle over the OCT needle to the identified depth; and (4) retract the OCT needle so that the tissue can be recovered and biopsied, following standard biopsy procedures.

As noted above, OCT imaging can be used to identify abnormal tissue. The following aspect of the concepts disclosed herein is a method for registering the location of abnormalities identified in OCT images, to enable the abnormalities to be localized for biopsy or therapy. Localization or registration techniques for use with identifying a particular portion of esophageal tissue location disclosed herein include laser marking, electrocauterization of a reference grid on the surface of the esophageal lumen, and ink tattooing.

Laser Marking and Therapy: A region of interest in the GI tract (e.g. the esophagus or the colon) can be identified in the OCT images during real time 3D balloon catheter imaging, or during fast playback while the catheter maintains its position relative to its initial position. Once the region of interest is identified, the balloon catheter can be positioned back at the region of interest or adjacent to the region of interest. Light from a high-power laser (such as a green yttrium aluminum garnet (YAG) laser) can be passed through the catheter and targeted at the region of interest (or its nearby region), creating a superficial cauterized mark on the surface of the esophageal lumen. The laser can be disposed externally, and coupled to the region of interest via optical fibers. If a laser of sufficient power is available having a sufficiently small form factor, the laser itself can be incorporated into the catheter. Multiple cauterized marks can be placed at or around the region of interest to allow the physician to visually target the region of interest for further biopsy or treatment, such as ablation or resection. The same procedure can be performed for other regions of interest.

A region of interest can be identified visually during real-time OCT imaging. This can be accomplished via computer tracking (i.e., an operator of the OCT system can instruct a computer system used to display the OCT images in real-time to keep track of a region of interest identified by the operator during real-time imaging), which will maintain a record of the image frames associated with each region of interest identified. Such a record preferably will include information about the relative positions of the regions of interest (e.g. the longitudinal distance from the initial position of the imaging beam). A region of interest can also be identified during playback mode (i.e., an operator of the OCT system can instruct a computer system used to display the OCT images during playback to keep track of a region of interest identified by the operator during playback). The catheter can then be moved back to regions near each region of interest under precise computer control, and the region of interest can be re-imaged while the OCT imaging catheter is precisely targeted at the region of interest. The high-power laser, which preferably employs the same optics as the OCT imaging beam, will deliver the laser energy to the target and generate the cauterized marks, which can then be used to guide a clinician back to the region of interest for biopsy, therapy or resection.

Particularly in embodiments wherein the laser light is delivered through the same optical fiber used for OCT imaging, the laser light can be delivered with great precision. FIG. 16 is a functional block diagram of an OCT system 240 incorporating a laser for marking a region of interest, where the laser light is delivered using the same optical fiber that is used for OCT imaging. Note the operator can select the light source going through coupler 242 either for OCT imaging or for marking a region of interest. The OCT catheter in FIG. 16 is used to locate a region of interest, and once located, a focal point of the OCT catheter is aimed at the region of interest, or immediately adjacent to the region of interest (in at least some embodiments, the region of interest is labeled by marking/delineating a proximal end and a distal end of the region of interest). Marking laser light is directed through beam coupler 242 into the OCT imaging optics, to create an ablation mark on the surface of the esophageal lumen (noting that if the catheter is employed in a different body lumen, then tissue associated with that other body lumen will be marked). It should be recognized that the laser can also be used to deliver targeted therapy to ablate the tissue at the region of interest under OCT image guidance. The OCT images can also be used to assess treatment response in real time (i.e., to determine whether the abnormal tissue has been completely ablated) by allowing both imaging light and marking light through coupler 242.

Electrocauterization Based Marking: In this technique, the exterior surface of a balloon catheter 244 (schematically shown in FIG. 17, alone with a guidewire 246) includes electrodes 248 configured to place grid markings on the surface of the esophageal lumen prior to OCT imaging (recognizing that the same technique can be used in other body lumens) via cauterization. While many patterns are possible, preferably electrodes 248 are disposed circumferentially about the surface of the balloon, with each electrode section being separated by known increments. The reference grid cauterized into the body lumen can be used during OCT imaging to identify a particular grid location corresponding to a region of interest.

Both monopolar and bipolar (also known as monothermy and diathermy, respectively) cauterization technologies can be employed. Both techniques involve high frequency alternating current and paired electrodes; a first electrode referred to as the active electrode and the other electrode referred to as the return electrode. The difference in the respective techniques lies in the placement of these electrodes. In monopolar cauterization current is passed from the active electrode (where cauterization occurs), and the patient's body serves as a ground. The return electrode (also referred to as a grounding pad) is placed on the person's body (often the thigh), and it carries the current back to the electrocauterization unit to complete the circuit. The return electrode must be monitored carefully to prevent burns, as extensive burns can occur undetected if the return electrode is not correctly positioned. In bipolar cauterization the active electrode and the return electrode are both disposed proximate the site of cauterization.

Ink/Tattooing Based Marking: The esophagus surface (or the surface of another body lumen) can be tattooed with small ink dots using standard endoscopy techniques. Many patterns of dots are possible. In an exemplary (but not limiting) embodiment, the dots form a pattern indicating a relative longitudinal distance along a body lumen, and a relative orientation on each cross-section. Such an exemplary tattoo pattern is shown in FIG. 18, in which dots 258, 260, 262 are used to mark a first cross section of body lumen 250 and dots 264, 266, and 268 are used to mark a second cross section of body lumen 250. Dots 258 and 264 are oriented at 12:00 o'clock, dots 260 and 266 are oriented at 1:00 o'clock, and dots 262 and 268 are oriented at 6:00 o'clock. Each dot can be identical, or if desired, different colors or shapes can be used to enable dots at different cross sections or different clock positions to be distinguished.

The dots will show up on the OCT images and can be used as the landmarks to identify the relative positions of various regions of interest (with respect to the dots). The relative positions can then be translated into the physical positions and used to guide the clinician to find a particular region of interest in the body lumen for subsequently performing biopsy, ablation, or resection.

An Exemplary Method for OCT-guided therapy: Using the OCT balloon catheter and a laser as shown in FIG. 16, OCT imaging system 240 can be used to identify abnormal structures such as high-grade dysplasia, intramucosal carcinoma, or subsquamous Barrett's metaplasia. Once the margins of a region of interest are identified, laser light can then be passed through the OCT catheter to ablate tissue at the region of interest. The treatment effects can then be immediately evaluated using OCT imaging (i.e., without removing the catheter) to assess the treatment response and determine if further ablation is necessary.

It should be noted that with respect to esophageal imaging, the OCT balloon probes disclosed above can not only examine esophageal surface tissue, but sub-squamous tissue as well. This is significant, because if only esophageal surface tissue is examined, then some Barrett's esophageal tissue (i.e., sub-squamous Barrett's tissue) could be missed. Because of the strong link between the presence of Barrett's esophageal tissue and an increased risk for esophageal cancer, it is desirable to systematically scan the esophagus for both surface Barrett's esophageal tissue and sub-squamous Barrett's esophageal tissue.

Another aspect of the concepts disclosed herein relates to a method for assessing the effectiveness of therapy for treating of Barrett's esophageal tissue. After the therapy has been performed (noting that in some embodiments disclosed herein, a single probe can be used to provide both OCT imaging and laser ablation therapy), OCT is used to examine each treatment site to determine if any Barrett's esophageal tissue remains under the squamous layers. This is an important step, as ablation therapy can eradicate Barrett's esophageal tissue at the surface of the esophagus, while leaving traces of sub-squamous Barrett's esophageal tissue.

Where specific dimensions are referred to above, it should be recognized that the disclosure is merely intended to be exemplary, and it is further intended to be broadly interpreted so as to encompass variations to such specifically identified parameters. Thus, such parameters should not be considered to be limiting, unless limitations are specifically recited in the claims that follow.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for performing optical coherence tomography (OCT), comprising the steps of:
   (a) advancing an OCT probe comprising an optical fiber and a compound lens to a position adjacent to a sample, wherein the compound lens includes a plurality of optical elements;
   (b) directing light from a distal end of the optical fiber through the compound lens, the compound lens being configured to focus light from the OCT probe at a predefined working distance, while enabling a smaller focused spot size to be achieved at the predefined working distance as compared to an OCT probe having a similar diameter that is configured to focus light at the predefined working distance using a single component lens, the step of directing light from the distal end of the optical fiber through the compound lens comprising the steps of:
      (i) directing light from the distal end of the optical fiber toward a beam adjusting element of the compound lens, the beam adjusting element being configured to manipulate light from the optical fiber so that a light beam exiting the beam adjusting element has a smaller beam diameter than a light beam exiting the distal end of the optical fiber, thus increasing a numerical aperture of the OCT probe relative to that at the distal end of the optical fiber; and
      (ii) directing light from the beam adjusting element to a distal lens element in the compound lens, the distal lens element being configured to focus light manipulated by the beam adjusting element at the predefined working distance proximate the sample;
   (c) collecting light received back from the sample; and
   (d) using light received back from the sample to generate OCT data.

2. The method of claim 1, wherein the step of directing light from the distal end of the optical fiber through the compound lens further comprises the step of directing light through the compound lens such that while propagating through the compound lens, light does not encounter a void between adjacent optical elements of the compound lens, and light does not encounter a beam deflector between adjacent optical elements of the compound lens.

3. The method of claim 1, wherein the beam adjusting element is further configured to focus light emitted by the distal end of the optical fiber to a spot disposed proximate a distal face of the beam adjusting element.

4. The method of claim 1, further comprising the step of marking a region of interest identified using the OCT data.

5. The method of claim 4, wherein the step of marking the region of interest comprises the step of directing laser light through the optical fiber and the compound lens, the laser light marking tissue at the region of interest.

6. The method of claim 4, wherein the step of marking the region of interest comprises the steps of:

(a) energizing electrodes disposed on an outer surface of a balloon encompassing a distal end of the OCT probe to mark adjacent tissue with a pattern; and
(b) documenting which portion of the pattern corresponds to the region of interest.

7. The method of claim 4, wherein the step of marking the region of interest comprises the step of marking the region of interest with an ink or dye.

8. The method of claim 1, further comprising the step of collimating the light from the optical fiber before the light is incident on the beam adjusting element.

9. The method of claim 1, wherein the step of directing light from the distal end of the optical fiber through the compound lens comprises the steps of:
   (a) directing light from the distal end of the optical fiber toward a first optical element that approximately collimates the light from the optical fiber; and
   (b) directing the light from the first optical element that has been collimated to the beam adjusting element.

10. The method of claim 1, wherein the step of directing light from the beam adjusting element to the distal lens element comprises the step of directing light into the distal lens element wherein the distal lens element has a larger aperture than the beam adjusting element.

11. An optical probe for use in high resolution optical coherence tomography (OCT), comprising:
   (a) an optical fiber; and
   (b) a compound lens having a plurality of individual elements, for focusing light from the optical fiber at a predefined working distance, while enabling a diameter of the optical probe to be reduced as compared to an optical probe configured to focus light at the predefined working distance using a single component lens, the compound lens comprising:
      (i) a beam adjusting element configured to manipulate light from the optical fiber so that a light beam exiting a distal end of the beam adjusting element has a smaller beam diameter than a light beam exiting the distal end of the optical fiber, thus increasing a numerical aperture of the OCT probe relative to that at the distal end of the optical fiber; and
      (ii) a distal lens element configured to focus light manipulated by the beam adjusting element at the predefined working distance proximate the sample.

12. The optical probe of Claim 11, wherein a diameter of the distal lens element is larger than a diameter of the beam adjusting element.

13. The optical probe of claim 11, wherein a diameter of the beam adjusting element is substantially equal to a diameter of the optical fiber.

14. The optical probe of claim 11, further comprising an optically transparent spacer disposed between a distal face of the optical fiber and a proximal face of the compound lens, the optically transparent spacer being thermally fused to the distal face of the optical fiber and the proximal face of the compound lens, the predefined working distance being a function of a length of the optically transparent spacer.

15. The optical probe of claim 11, wherein the beam adjusting element and the distal lens element each comprise a gradient index (GRIN) lens, the beam adjusting element and the distal lens element are adhesively coupled together using optical cement, and the beam adjusting element is thermally fused to at least one of the optical fiber and an optically transparent spacer that is disposed between the optical fiber and the beam adjusting element.

16. The optical probe of claim 11, wherein the compound lens further comprises a proximal GRIN lens disposed between the optical fiber and beam adjusting element, the proximal GRIN lens substantially collimating light from the optical fiber.

17. The optical probe of claim 16, wherein diameters of the optical fiber, the proximal GRIN lens, and the beam adjusting element are:
   (a) substantially the same; and
   (b) smaller than a diameter of the distal lens element.

18. The optical probe of claim 16, wherein an α-value of the beam adjusting element is larger than an α-value of the proximal GRIN lens and an α-value of the distal lens element.

19. The optical probe of claim 16, wherein a pitch of at least one of the beam adjusting element, the proximal GRIN lens, and the distal lens element is different than a pitch of another one of the beam adjusting element, the proximal GRIN lens, and the distal lens element.

20. The optical probe of claim 11, wherein the probe further comprises a beam coupler enabling a light source used for OCT imaging to be switched with a laser light source to be used to mark a region of interest or to perform ablation therapy.

21. The optical probe of claim 11, wherein the probe comprises an outer metal needle housing, and an inner transparent housing, a distal end of the optical fiber and the compound lens being disposed within the inner transparent housing.

22. The optical probe of claim 11, wherein the probe comprises an outer metal needle housing and an optically transparent window, a distal end of the optical fiber and the compound lens being disposed to direct light through the optically transparent window.

23. A system for carrying out high resolution optical coherence tomography (OCT) of a body lumen, comprising:
   (a) a low-coherence light source;
   (b) a sample arm comprising an OCT probe configured to scan a sample in the body lumen, the sample arm exhibiting a first optical path length and being optically coupled to the light source, the OCT probe having a form factor suitable for body lumen imaging, and including an optical fiber and a compound lens, the compound lens comprising:
      (i) a beam adjusting element configured to manipulate light from the optical fiber so that a light beam exiting a distal end of the beam adjusting element has a smaller beam diameter than a light beam exiting the distal end of the optical fiber, thus increasing a numerical aperture of the OCT probe relative to that at the distal end of the optical fiber; and
      (ii) a distal lens element configured to focus light manipulated by the beam adjusting element at the predefined working distance proximate the sample;
   (c) a reference arm exhibiting a second optical path length, the reference arm being optically coupled to the light source;
   (d) a detector optically coupled to the sample arm and the reference arm;
   (e) a prime mover and a fiber optic rotary joint disposed at a proximal end of the OCT probe, the rotary joint cooperating with the prime mover to enable the optical fiber to be selectively rotated;
   (f) a linear translation component, enabling the OCT probe to be selectively linearly translated relative to the sample; and
   (g) a processor and memory logically coupled to the detector, the OCT probe, the prime mover and the translation component, the processor being configured to execute a plurality of machine instructions stored in the memory, to carry out at least one of the following functions:

(i) controlling the prime mover and the OCT probe to implement a circumferential scanning of the body lumen; and
(ii) controlling the prime mover, the linear translation component and the OCT probe to enable a three dimensional spiral imaging of the body lumen to be achieved.

24. The system of claim 23, further comprising a beam coupler enabling the low coherence light source to be switched with a laser light source to be used to mark a region of interest or to perform ablation therapy.

25. An optical probe for use in high resolution optical coherence tomography (OCT) guided needle biopsy, comprising:
(a) a metal needle housing including an opening through which light can pass, the opening being disposed at a distal end of the metal needle housing;
(b) an optical fiber; and
(c) an optical element for focusing light from the optical fiber at a predefined working distance, wherein at least one of the following is true:
(i) the optical element comprises a compound lens; including:
(A) a beam adjusting element configured to manipulate light from the optical fiber so that a light beam exiting a distal end of the beam adjusting element has a smaller beam diameter than a light beam exiting the distal end of the optical fiber, thus increasing a numerical aperture of the OCT probe relative to that at the distal end of the optical fiber; and
(B) a distal lens element configured to focus light manipulated by the beam adjusting element at the predefined working distance proximate the sample; and
(ii) the optical element and a distal end of the optical fiber are encapsulated in an inner optically transmissive housing, the inner optically transmissive housing being disposed within the metal needle housing.

26. An optical probe for use in high resolution optical coherence tomography (OCT), comprising:
(a) an optical fiber; and
(b) a beam focusing structure comprising a plurality of optical elements including at least one gradient index (GRIN) lens, a proximal optical element in the beam focusing structure being thermally fused to a distal end of the optical fiber, wherein the beam focusing structure comprises a compound lens including a GRIN lens configured to manipulate light from the optical fiber so that a light beam exiting a distal end of the beam adjusting element has a smaller beam diameter than a light beam exiting the distal end of the optical fiber, thus increasing a numerical aperture of the OCT probe relative to that at the distal end of the optical fiber.

27. The optical probe of claim 26, wherein the proximal optical element includes an optically transparent spacer, a distal end of which is thermally fused to a proximal end of one GRIN lens.

28. The optical probe of claim 26, wherein the proximal optical element comprises a first GRIN lens, a distal end of the first GRIN lens being thermally fused to a proximal end of a second GRIN lens, a distal end of the second GRIN lens being adhesively coupled to a proximal end of a third GRIN lens using one of an optical cement or thermal fusion.

29. An optical probe for use in high resolution optical coherence tomography (OCT) guided needle biopsy, comprising:
(a) a metal needle housing including an opening through which light can pass, the opening being disposed at a distal end of the metal needle housing;
(b) an optical fiber; and
(c) an optical element for focusing light from the optical fiber at a predefined working distance, wherein at least one of the following is true:
(i) the optical element comprises a compound lens including:
(A) a first optical element configured to collimate light emitted from the distal end of the optical fiber;
(B) a second optical element configured to receive the light that was collimated and to focus the light that was collimated to a spot smaller than a diameter of the beam from the optical fiber, the spot being proximate a distal face of the second optical element, an $\alpha$-value of the second optical element being larger than an $\alpha$-value of the first optical element; and
(C) a third optical element configured to receive light from the second optical element and to focus light from the OCT probe at the predefined working distance, the third optical element having a larger aperture than the second element, but a smaller $\alpha$-value than the second optical element; and
(ii) the optical element and a distal end of the optical fiber are encapsulated in an inner optically transmissive housing, the inner optically transmissive housing being disposed within the metal needle housing.

* * * * *